(12) United States Patent
Herold et al.

(10) Patent No.: US 7,767,690 B2
(45) Date of Patent: Aug. 3, 2010

(54) AMINO ALCOHOL DERIVATIVES AND THEIR USE AS RENIN INHIBITOR

(75) Inventors: Peter Herold, Basel (CH); Stefan Stutz, Basel (CH); Aleksandar Stojanovic, Basel (CH); Vincenzo Tschinke, Binningen (CH); Christiane Marti, Baden (CH); Michael Quirmbach, Basel (CH)

(73) Assignee: Novartis AG, Basel (CH)

( * ) Notice: Subject to any disclaimer, the term of this patent is extended or adjusted under 35 U.S.C. 154(b) by 815 days.

(21) Appl. No.: 10/587,046

(22) PCT Filed: Jan. 21, 2005

(86) PCT No.: PCT/EP2005/050273

§ 371 (c)(1),
(2), (4) Date: Jul. 24, 2006

(87) PCT Pub. No.: WO2005/070870

PCT Pub. Date: Aug. 4, 2005

(65) Prior Publication Data

US 2009/0118281 A1      May 7, 2009

(30) Foreign Application Priority Data

Jan. 23, 2004   (CH) .................... 0095/04

(51) Int. Cl.
*A61K 31/435*   (2006.01)
*C07D 221/04*   (2006.01)
(52) U.S. Cl. .............. 514/299; 546/112; 546/184; 514/315
(58) Field of Classification Search ............. 546/112, 546/184; 514/299, 315
See application file for complete search history.

(56) References Cited

FOREIGN PATENT DOCUMENTS

WO      02/40007      5/2002

OTHER PUBLICATIONS

P. Raddatz et al., "Renin Inhibitors Containing New P1-P1'Dipeptide Mimetics with Heterocycles in P1'", Journal of Medicinal Chemistry, American Chemical Society, vol. 35, No. 19, pp. 3525-3536, XP002050635, ISSN: 0022-2623, Sep. 18, 1992.
K. Allikmets, "Aliskiren Speedel", Current Opinion in Investigational Drugs, Pharmapress, U.S., vol. 3, No. 10, pp. 1479-1482, XP009017210, ISSN: 1472-4472, 2002.
J.M. Wood et al., "Structure-based design of aliskiren, a novel orally effective renin inhibitor", Biochemical and Biophysical Research Communications, Academic Press Inc., vol. 308, No. 4, pp. 698-705, XP004447169, ISSN: 0006-291X, Sep. 5, 2003.

*Primary Examiner*—Golam M Shameem
(74) *Attorney, Agent, or Firm*—Wenderoth, Lind & Ponack, L.L.P.

(57) ABSTRACT

The application relates to novel amino alcohols of the general formula (I) where R, $R_1$, $R_2$, $R_3$, $R_4$, $R_5$ and $R_6$ each have the definitions illustrated in detail in the description, to a process for their preparation and to the use of these compounds as medicines, in particular as renin inhibitors.

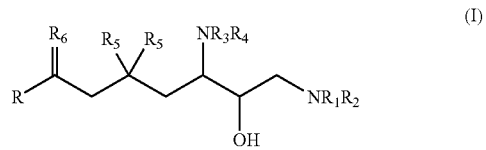

(I)

12 Claims, No Drawings

AMINO ALCOHOL DERIVATIVES AND THEIR USE AS RENIN INHIBITOR

The invention relates to novel amino alcohols, to processes for preparing the inventive compounds, to pharmaceutical preparations comprising them and to their use as medicaments, in particular as renin inhibitors.

Amino-compounds showing renin-inhibiting properties are known, for example from EP519433.

Firstly, the present invention provides compounds of the general formula

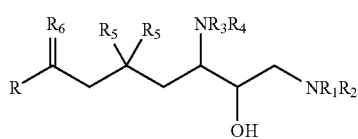

where $R_1$ is a) hydrogen, amino or hydroxyl; or is b) $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4, $C_1$-$C_8$-alkyl, halogen, cyano, oxide, oxo, trifluoromethyl, $C_1$-$C_8$-alkoxy, $C_1$-$C_8$-alkoxycarbonyl, aryl or heterocyclyl;

$R_2$ is a) $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_8$-cycloalkyl-$C_1$-$C_8$-alkanoyl, aryl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_{12}$-cycloalkyl, $C_3$-$C_8$-cycloalkoxy, amino, $C_1$-$C_6$-alkylamino, di-$C_1$-$C_6$-alkylamino, $C_1$-$C_6$-alkanoylamino, $C_1$-$C_6$-alkoxycarbonylamino, halogen, oxo, cyano, hydroxyl, oxide, trifluoromethyl, $C_1$-$C_8$-alkoxy, optionally N-mono- or N,N-di-$C_1$-$C_8$-alkylated carbamoyl-$C_0$-$C_8$-alkyl, optionally esterified carboxyl, $C_1$-$C_6$-alkylenedioxy, aryl or heterocyclyl; or is b) together with $R_1$ and the nitrogen atom to which they are bonded a saturated or partly unsaturated 4-8-membered heterocyclic ring which may contain an additional nitrogen, oxygen or sulphur atom or a —SO— or —SO2- group, in which case the additional nitrogen atom may optionally be substituted by $C_1$-$C_8$-alkyl, $C_1$-$C_8$-alkanoyl, $C_1$-$C_8$-alkoxycarbonyl, aryl or heterocyclyl radicals, and this heterocyclic ring may be part of a bicyclic or tricyclic ring system having a total of up to 16 members and the second ring may also contain a nitrogen, oxygen or sulphur atom or a —SO— or —SO2- group, and the nitrogen atom in the second ring may optionally be substituted by $C_1$-$C_8$-alkyl, $C_1$-$C_8$-alkanoyl, $C_1$-$C_8$-alkoxycarbonyl, aryl or heterocyclyl radicals and all ring systems mentioned may be substituted by 1-4 $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_8$-cycloalkyl-$C_1$-$C_8$-alkanoyl, aryl-$C_1$-$C_8$-alkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, halogen, hydroxyl, oxide, oxo, trifluoromethyl, $C_1$-$C_8$-alkoxy, $C_1$-$C_8$-alkoxy-$C_1$-$C_8$-alkoxy, $C_1$-$C_8$-alkoxy-$C_1$-$C_8$-alkyl, $C_1$-$C_8$-alkoxycarbonylamino, $C_1$-$C_8$-alkanoylamino, $C_1$-$C_8$-alkyl-amino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy or heterocyclyloxy-$C_0$-$C_4$-alkyl-$C_1$-$C_8$-alkoxy;

$R_3$ is hydrogen, $C_1$-$C_8$-alkyl, $C_1$-$C_8$-alkoxycarbonyl or $C_1$-$C_8$-alkanoyl;

$R_4$ is hydrogen, $C_1$-$C_8$-alkyl, $C_1$-$C_8$-alkoxycarbonyl or $C_1$-$C_8$-alkanoyl;

$R_6$ are each independently hydrogen or $C_1$-$C_8$-alkyl or, together with the carbon atom to which they are bonded, are a $C_0$-$C_8$-cycloalkylidene radical;

$R_6$ is one oxygen atom or two hydrogen atoms;

R is optionally suited arylamino, N-aryl-N-(lower alkoxy)(lower alkyl))amino, N-aryl-N-aryl(lower alkyl)amino or heterocyclyl bonded via a ring nitrogen atom;

and salts thereof.

The asymmetric carbon atoms present in compounds of the formula (I) may have R—, S— or R,S-configurations. Accordingly, the compounds present may occur as isomer mixtures or as pure isomers, in particular as diastereoisomer mixtures, enantiomer pairs or pure enantiomers.

In the context of the restrictions specified for the substituents of the formula (I), the individual substituents are defined as follows:

Aryl, and aryl in arylamino, aryl-$C_0$-$C_4$-alkyl, aryl(lower alkyl), N-aryl-N-(lower alkoxy)(lower alkyl)amino, N-aryl-N-aryl(lower alkyl)amino, contains generally 1-14, preferably 6-10 carbon atoms, and is, for example, phenyl, indenyl, e.g. 2- or 4-indenyl, or naphthyl, e.g. 1- or 2-naphthyl. Preference is given to aryl having 6-10 carbon atoms, in particular phenyl or 1- or 2-naphthyl. The radicals mentioned may be unsubstituted or, for example, mono- or polysubstituted, for example mono- or disubstituted, by a lower alkyl, hydroxyl, lower alkoxy, oxo, carbamoyl(lower alkoxy), $C_3$-$C_8$-cycloalkyl, $C_1$-$C_8$-alkylsulphonyl, $C_3$-$C_8$-cycloalkylsulphonyl, aryl-$C_0$-$C_0$-alkylsulphonyl, heterocyclylsulphonyl, $C_3$-$C_8$-cycloalkyl-$C_1$-$C_8$-alkanoyl, aryl-$C_1$-$C_8$-alkanoyl, $C_1$-$C_8$-alkanoyl, $C_1$-$C_8$-alkoxycarbonyl, optionally N-mono- or N,N-di-$C_1$-$C_8$-alkylated carbamoyl-$C_1$-$C_8$-alkyl, (lower alkyl) carbamoyl(lower alkoxy), di(lower alkyl) carbamoyl(lower alkoxy), amino, (lower alkyl)- or di(lower alkyl)amino, carboxyl, (lower alkoxy)carbonyl, carbamoyl, sulphamoyl, (lower alkane)sulphonyl, halogen, trifluoromethyl, nitro, phenyl, 5- or 6-membered heterocyclyl containing as a heteroatom 1 nitrogen, sulphur or oxygen atom, 2 nitrogen atoms, 1 nitrogen atom and 1 sulphur atom, or 1 nitrogen atom and 1 oxygen atom, such as pyridyl, and/or by cyano, and the substituent may be present in any position, for example the o-, m- or p-position of the phenyl radicals, or in the 3- or 4-position of the 1- or 2-naphthyl radical, and a plurality of identical or different substituents may also be present.

Arylamino is, for example, anilino or 1- or 2-naphthylamino which are each unsubstituted or substituted in the phenyl or naphthyl moiety as specified above.

Heterocyclyl, and heterocyclyl in heterocyclyl-$C_0$-$C_4$-alkyl has, for example, from 5 to 7 ring atoms in the heterocyclyl ring and may contain one ring nitrogen atom and/or one further ring heteroatom selected from oxygen, sulphur and nitrogen, is, for example, furanyl, tetrahydrofuranyl, pyranyl, tetrahydropyranyl, thiazolyl, oxazolyl, pyridinyl or imidazolyl which are each unsubstituted or substituted by $C_1$-$C_8$-alkyl, halogen, oxo, oxide, cyano, trifluoromethyl, $C_1$-$C_8$-alkoxy, $C_1$-$C_8$-alkanoyl, $C_1$-$C_8$-alkoxycarbonyl, aryl or heterocylyl.

Heterocyclyl-$C_0$-$C_4$-alkyl is, for example, pyridinyl, methylenepyridinyl or imidazolyl.

In the case of nitrogen heterocycles, the heterocyclyl radicals can be bonded either via the nitrogen or via a ring carbon.

Heterocyclyl bonded via a ring nitrogen atom and having from 4 to 8 ring atoms has in particular from 5 to 7 ring atoms and may have 1 or 2 fused-on phenyl or cycloalkyl radicals, or else be present as a spiro compound. Examples include pyrrolidino, piperidino, piperazine, morpholino, thiomorpholino, indolin-1-yl, isoindolin-2-yl, 2,3-dihydrobenzimidazol-1-yl, 1,2,3,4-tetrahydroquinol-1-yl, 1,2,3,4-tetrahydroisoquinol-2-yl, 1,2,3,4-tetrahydro-1,3-benzodiazin-1-yl or -3-yl, 1,2,3,4-tetrahydro-1,4-benzodiazin-1-yl, 3,4-dihydro-2H-1,4-benzoxazin-4-yl, 3,4-dihydro-2H-1,4-benzothiazin-4-yl, 3,4-dihydro-2H-1,3-benzothiazin-1-yl, 3,4,5,6,7,8-hexahydro-2H-1,4-benzoxazin-4-yl, 3,4,5,6,7,8-hexahydro-2H-1,4-benzothiazin-4-yl, 2,3,4,5-tetrahydro-1H-1-benz[6,7-b]azepin-1-yl and 5,6-dihydrophenanthridin-5-yl. Preference is given to benzofused 5- to 7-membered aza-, diaza-, azoxa- and azathiacycloalkenyl radicals bonded via a nitrogen atom, in particular indolin-1-yl, 1,2,3,4-tetrahydroquinolin-1-yl, 1,2,3,4-tetrahydroisoquinolin-2-yl, 1,2,3,4-tetrahydro-1,3-benzodiazin-1-yl, 1,2,3,4-tetrahydro-1,4-benzodiazin-1-yl, 3,4-dihydro-2H-1,4-benzoxazin-4-yl, 3,4-dihydro-2H-1,4-benzothiazin-4-yl, 3,4-dihydro-2H-1,3-benzothiazin-1-yl and 2,3,4,5-tetrahydro-1H-1-benz[6,7-b]azepin-1-yl. Further preferred for —$NR_1R_2$ are in particular pyrrolidino, piperidino, morpholino, 9-azabicyclo[3.3.1]non-9-yl, 1-azepan-1-yl, 2,8-diazaspiro[4.5]dec-8-yl, octahydroisoindol-2-yl, 4-azatricyclo[5.2.1.0$^{2,6}$]dec-4-yl, 3-azabicyclo[3.2.1]oct-3-yl, 3,7-diazabicyclo[3.3.1]non-3-yl, 3-azabicyclo[3.3.1]non-3-yl, 8-azabicyclo[3.2.1]oct-8-yl, 3-azabicyclo[3.2.2]non-3-yl and tetrahydro-1H-1-benz[6,7-b]azepin-1-yl.

The radicals mentioned may be unsubstituted or N-substituted and/or C-substituted, in which case in particular 1, 2 or 3 substituents may be present.

Examples of useful nitrogen substituents are, for example, lower alkyl, lower alkanoyl, (lower alkoxy)carbonyl, (lower alkane)sulphonyl, oxide, aryl or heteroaryl. Carbon substituents are, for example, lower alkyl, hydroxy(lower alkyl), (lower alkoxy)(lower alkyl), (lower alkenyl)oxy(lower alkyl), naphthoxy(lower alkyl), phenyloxy(lower alkyl), phenyl(lower alkoxy)(lower alkyl), (lower alkanoyl)oxy(lower alkyl), benzoyloxy(lower alkyl), (lower alkoxy)carbonyloxy (lower alkyl), phenyloxycarbonyloxy(lower alkyl), phenyl (lower alkoxy)carbonyloxy(lower alkyl), amino(lower alkyl), N-(lower alkyl)amino(lower alkyl), N,N-di(lower alkyl)amino(lower alkyl), carbamoyl(lower alkyl), (lower alkanoyl)amino(lower alkyl), benzoylamino(lower alkyl), (lower alkoxy)carbonylamino(lower alkyl), (lower alkoxycarbonyl(lower alkyl), (lower alkoxy)(lower alkoxy)(lower alkyl), (lower alkyl)thio(lower alkoxy)(lower alkyl), N-(lower alkoxy)imino(lower alkyl), cycloalkoxy(lower alkyl), cycloalkyl(lower alkoxy)(lower alkyl), lower alkenyl, (lower alkenyl)oxy, (lower alkoxy)(lower alkenyl), lower alkynyl, (lower alkynyl)oxy, lower alkanoyl, oxo, hydroxy, lower alkoxy, carbamoyl(lower alkoxy), N-(lower alkyl)carbamoyl(lower alkoxy), N-(lower alkyl) carbamoyloxy, N,N-di(lower alkyl)carbamoyloxy, (lower alkoxy)(lower alkoxy), (lower alkyl)thio(lower alkoxy), (lower alkanoyl)oxy, benzoyloxy, N-(lower alkyl)carbamoyl, amino, N-(lower alkyl) amino, N,N-di(lower alkyl)amino, (lower alkanoyl)amino, benzoylamino, cycloalkylcarbonylamino, cycloalkyl(lower alkanoyl)amino, (lower alkoxy)carbonyl(lower alkyl)amino, (lower alkenyl)oxycarbonylamino, (lower alkoxy)(lower alkoxy)carbonylamino, (lower alkoxy)(lower alkanoyl) amino, N-(lower alkyl)carbamoylamino, N,N-di(lower alkyl)-carbamoylamino, N-(lower alkanoyl)-N-(lower alkyl) amino, (lower alkoxy)carbonylamino, N-lower alkoxy)carbonyl-N-(lower alkyl)amino, N,N-(lower alkylene)amino, N,N-(1-oxo(lower alkylene))amino, N,N-(1-oxo-2-oxa (lower alkylene))amino, carboxy, (lower alkoxy)carbonyl, phenyl(lower alkoxy)carbonyl, phenyloxycarbonyl, pyrrolidinylcarbonyl, piperidinylcarbonyl, piperazinylcarbonyl, morpholinylcarbonyl, thiomorpholinyicarbonyl, S,S-dioxothiomorpholin-4-ylcarbonyl, cyano, carbamoyl, N,N-di (lower alkyl)carbamoyl, N-(lower alkenyl)carbamoyl, N-cycloalkylcarbamoyl, N-cycloalky(lower alkyl)carbamoyl, N-hydroxy(lower alkyl)carbamoyl, N-(lower alkoxy)(lower alkyl)carbamoyl, N-carboxy(lower alkyl)carbamoyl, carbamoyl(lower alkyl)carbamoyl, (lower alkoxy)carbonyl (lower alkyl)carbamoyl, phenyl, dioxolan-2-yl, oxazol-2-yl, oxazolin-2-yl, oxazolidin-2-yl, nitro, sulphamoyl, (lower alkane)sulphonyl, phosphono, (lower alkane)phosphono, di(lower alkyl)phosphono, polyhalo(lower alkyl) and halogen.

The compound groups mentioned below are not to be regarded as dosed, but rather it is possible in a sensible manner to exchange parts of these compound groups with one another or with the definitions given above, or to omit parts, for example to replace general by more specific definitions.

Preference is given to compounds of the formula (I) where $R_6$ is oxygen.

Particularly preferred R radicals are bicyclic radicals of the formula (Ia)

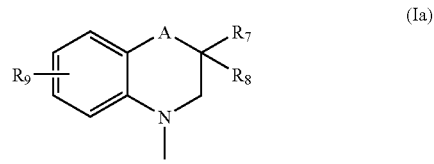

(Ia)

where A is a direct bond, methylene, dimethylene, imino, oxy or thio, $R_7$ is (lower alkoxy)(lower alkyl), (lower alkenyl)oxy (lower alkyl), (lower alkoxy)(lower alkoxy)(lower alkyl), (lower alkoxy)carbonylamino(lower alkyl), N-(lower alkoxy)imino(lower alkyl), phenyl, (lower alkoxy)carbonyl, cyano, carbamoyl, N-(lower alkyl)carbamoyl, N-((lower alkoxy)(lower alkyl))carbamoyl, (lower alkoxy), (lower alkoxy)(lower alkoxy), (lower alkanoyl)oxy, benzoyloxy, (lower alkanoyl)amino, (lower alkoxy)carbonylamino, 3- to 6-membered cycloalkylcarbonylamino, N-((lower alkoxy) (lower alkanoyl))amino, N-((lower alkyl)-carbamoyl)amino, N,N-(1-oxo(lower alkylene))amino, or N,N-(1-oxo-2-oxa (lower alkylpene))amino, $R_8$ is hydrogen or lower alkyl and $R_9$ is hydrogen or halogen.

Above and below, "lower" radicals and compounds refer, for example, to those which have up to and including 8, preferably up to and including 4, carbon atoms.

$C_1$-$C_8$-alkylenedioxy is, for example, methylenedioxy or ethylenedioxy, but may also be 1,3- or 1,2-propylenedioxy.

Aryl-$C_1$-$C_8$-alkanoyl is one of the aryl radicals mentioned which is bonded to the rest of the compound via a $C_1$-$C_8$-alkanoyl group, for example phenylformyl, phenylacetyl, 3-phenylpropionyl, 2-phenyl-2-methylpropionyl or phenylpivaloyl.

Aryl-$C_3$-$C_8$-cycloalkanoyl is one of the aryl radicals mentioned which is bonded to the rest of the compound via a $C_3$-$C_8$-cycloalkanoyl group, for example 1-phenycyclobutanoyl.

Aryl(lower alkyl) is, for example, phenyl- or naphthyl (lower alkyl) which are each unsubstituted or substituted in the phenyl or naphthyl moiety as specified above.

Aryl-$C_0$-$C_8$-alkylsulphonyl is one of the aryl radicals mentioned which is bonded to the rest of the compound either via a sulphonyl group or via a $C_1$-$C_8$-alkylsulphonyl group, for example phenylsulphonyl, benzylsulphonyl or phenyldimethylenesulphonyl.

Optionally esterified carboxyl is, for example, carboxyl esterified with $C_0$-$C_6$-alkyl, such as carboxyl or $C_1$-$C_6$-alkoxycarbonyl.

Cycloalkoxy(lower alkyl) is, for example, $C_3$-$C_8$-cycloalkoxy-$C_1$-$C_4$-alkyl, such as cyclopropyloxy-$C_1$-$C_4$-alkyl, cyclopentyloxy-$C_1$-$C_4$-alkyl or cyclohexyloxy-$C_1$-$C_4$-alkyl, in particular cyclopropyloxymethyl.

Cycloalkoxy is, for example, $C_3$-$C_8$-cycloalkoxy, such as cyclopropyloxy, cyclopentyloxy or cyclohexyloxy, in particular cyclopropyloxy.

Cycloalkyl is, for example, 3- to 12-, in particular 3- to 6-membered cycloalkyl, such as cyclopropyl, cyclobutyl, cyclopentyl, cyclohexyl or adamantyl.

Cycloalkylidene is, for example, 3 to 8-, in particular 3- to 6-membered cycloalkylidene, such as cyclopropylidene, cyclobutylidene, cyclopentylidene or cyclohexylidene.

Cycloalkyl(lower alkyl) is, for example, 3- to 8-, in particular 3- to 6-membered cycloalkyl(lower alkyl), such as cyclopropyl-, cyclobutyl-, cyclopentyl- or cyclohexyl(lower alkyl).

N-aryl-N-(lower alkoxy)(lower alkyl)amino is, for example, N-phenyl- or N-naphthyl-N-(lower alkoxy)(lower alkyl)amino which are each unsubstituted or substituted in the phenyl or naphthyl moiety as specified above.

N-aryl-N-aryl(lower alkyl)amino is, for example, N-phenyl- or N-naphthyl-N-(phenyl(lower alkyl))amino which are each unsubstituted or substituted in the phenyl or naphthyl moiety as specified above.

Cycloalkyl(lower alkanoyl) is, for example $C_3$-$C_8$-cycloalkyl-$C_1$-$C_4$-alkanoyl, such as cyclo-propyl-$C_1$-$C_4$-alkanoyl, cyclopentyl-$C_1$-$C_4$-alkanoyl or cyclohexyl-$C_1$-$C_4$-alkanoyl, in particular cyclopropylacetyl.

$C_3$-$C_8$-cycloalkylsulphonyl is, for example, cyclopentylsulphonyl, cyclohexylsulphonyl or cycloheptylsulphonyl, and also cyclopropylsulphonyl, cyclobutylsulphonyl or cyclooctylsulphonyl.

Halogen is, for example, fluorine, chlorine, bromine or iodine, preferably fluorine and chlorine.

Heterocyclyl-$C_0$-$C_4$-alkyl is one of the heterocyclyl radicals mentioned which is bonded to the rest of the compound either directly or via a $C_1$-$C_4$-alkyl group.

Heterocyclylsulphonyl is one of the heterocyclyl radicals mentioned which is bonded to the rest of the compound via a sulphonyl group.

Lower alkanoyl is, for example, $C_1$-$C_8$-alkanoyl, in particular $C_1$-$C_4$-alkanoyl, such as formyl, acetyl, propionyl, butyryl or pivaloyl. Lower alkanoyl $R_3$ is in particular formyl, acetyl, propionyl, butyryl, isobutyryl or pivaloyl.

(Lower alkanoyl)amino is, for example, $C_1$-$C_8$-alkanoylamino, in particular $C_1$-$C_4$-alkanoylamino, such as acetylamino, propionylamino, butyrylamino or pivaloylamino.

(Lower alkanoyl)amino(lower alkyl) is, for example, $C_1$-$C_8$-alkanoylamino-$C_1$-$C_4$-alkyl, in particular $C_1$-$C_4$-alkanoylamino-$C_1$-$C_4$-alkyl, such as formylaminomethyl, acetylaminomethyl, propionylaminomethyl, butyrylaminomethyl, pivaloylaminomethyl, 2-formylaminoethyl, 2-acetylaminoethyl, 2-propionylaminomethyl, 2-butyrylaminoethyl or 2-pivaloylaminoethyl.

N-(lower alkanoyl)-N-(lower alkyl)amino is, for example, N—($C_1$-$C_8$-alkanoyl)-N-($C_1$-$C_4$-alkyl)amino, in particular N—($C_1$-$C_4$-alkanoyl)-N-($C_1$-$C_4$-alkyl)amino, such as N-formyl-N-methylamino, N-acetyl-N-methylamino, N-propionyl-N-methylamino or N-butyryl-N-methyl-amino.

(Lower alkyl)sulphonyl is, for example, $C_1$-$C_8$-alkylsulphonyl, in particular $C_1$-$C_4$-alkyl-sulphonyl, such as methylsulphonyl, ethylsulphonyl, propylsulphonyl, prop-2-ylsulphonyl, butylsulphonyl, 2-methylpropylsulphonyl, but-2-ylsulphonyl or 2,2-dimethylethylsulphanyl.

Lower alkenyl is, for example, $C_2$-$C_8$-alkenyl, in particular $C_3$-$C_5$-alkenyl, such as allyl.

Lower alkynyl is, for example, $C_3$-$C_8$-alkynyl, in particular $C_3$-$C_5$-alkynyl, such as propargyl.

Lower alkoxy is, for example, $C_1$-$C_8$-alkoxy, in particular $C_1$-$C_4$-alkoxy, such as methoxy, ethoxy, propyloxy, isopropyloxy, butyloxy, isobutyloxy, sec-butyloxy or tert-butyloxy, but may also be a $C_5$-$C_8$-alkoxy group, such as a pentyloxy, hexyloxy or heptyloxy group.

(Lower alkoxy)carbonyl is, for example, $C_1$-$C_8$-alkoxycarbonyl, in particular $C_1$-$C_4$-alkoxycarbonyl, such as methoxycarbonyl, ethoxycarbonyl, propyloxycarbonyl, isopropyloxycarbonyl, butyloxycarbonyl, isobutyloxycarbonyl, sec-butyloxycarbonyl or tert-butyloxy-carbonyl.

(Lower alkoxy)carbonylamino is, for example, $C_1$-$C_8$-alkoxycarbonylamino, in particular $C_1$-$C_4$-alkoxycarbonylamino, such as methoxycarbonylamino, ethoxycarbonylamino, propyl-oxycarbonylamino, isopropyloxycarbonylamino or butyloxycarbonylamino.

(Lower alkoxy)(lower alkanoyl)amino is, for example, $C_1$-$C_4$-alkoxy-$C_1$-$C_4$-alkanoylamino, such as methoxy-$C_1$-$C_4$-alkanoylamino, ethoxy-$C_1$-$C_4$-alkanoylamino, propyloxy-$C_1$-$C_4$-alkanoylamino, isopropyloxy-$C_1$-$C_4$-alkanoylamino or butyloxy-$C_1$-$C_4$alkanoylamino, where $C_1$-$C_4$-alkanoyl is, for example, acetyl, propionyl or butyryl.

(Lower alkoxy)(lower alkoxy) is, for example, $C_1$-$C_8$-alkoxy-$C_1$-$C_4$-alkoxy, in particular $C_1$-$C_4$-alkoxy-$C_1$-$C_4$-alkoxy, such as methoxy-$C_1$-$C_4$-alkoxy, ethoxy-$C_1$-$C_4$-alkoxy, propyloxy-$C_1$-$C_4$-alkoxy, isopropyloxy-$C_1$-$C_4$-alkoxy, butyloxy-$C_1$-$C_4$-alkoxy, isobutyloxy-$C_1$-$C_4$-alkoxy, sec-butyloxy-$C_1$-$C_4$-alkoxy or tert-butyloxy-$C_1$-$C_4$-alkoxy, where $C_1$-$C_4$-alkoxy is, for example, methoxy, ethoxy, propyloxy or butyloxy, in particular methoxy- or ethoxymethoxy or 2-(methoxy)- or 2-(ethoxy)ethoxy.

(Lower alkoxy)(lower alkoxy)(lower alkyl) is, for example, $C_1$-$C_8$-alkoxy-$C_1$-$C_4$-alkoxy-$C_1$-$C_4$-alkyl, in particular $C_1$-$C_4$-alkoxy-$C_1$-$C_4$-alkoxy-$C_1$-$C_4$-alkyl, such as methoxy-$C_1$-$C_4$-alkoxy-$C_1$-$C_4$-alkyl, ethoxy-$C_1$-$C_4$-alkoxy-$C_1$-$C_4$-alkyl, propyloxy-$C_1$-$C_4$-alkoxy-$C_1$-$C_4$-alkyl, isopropyloxy-$C_1$-$C_4$-alkoxy-$C_1$-$C_4$-alkyl or butyloxy-$C_1$-$C_4$-alkoxy-$C_1$-$C_4$-alkyl, where $C_1$-$C_4$-alkoxy is, for example, methoxy, ethoxy, propyloxy or butyloxy and $C_1$-$C_4$-alkyl is, for example, methyl, ethyl, propyl or butyl, in particular 2-methoxyethoxymethyl.

(Lower alkoxy)(lower alkyl) is, for example, $C_1$-$C_8$-alkoxy-$C_1$-$C_4$-alkyl, in particular $C_1$-$C_4$-alkoxy-$C_1$-$C_4$-alkyl, such as methoxy-$C_1$-$C_4$-alkyl, ethoxy-$C_1$-$C_4$-alkyl, propyloxy-$C_1$-$C_4$-alkyl, isopropyloxy-$C_1$-$C_4$-alkyl, butyloxy-$C_1$-$C_4$-alkyl, -isobutyloxy-$C_1$-$C_4$-alkyl, sec-butyloxy-$C_1$-$C_4$-alkyl or tert-butyloxy-$C_1$-$C_4$-alkyl, where $C_1$-$C_4$-alkyl is, for example, methyl, ethyl, propyl or butyl, in particular ethoxymethyl.

Lower alkyl is branched or unbranched and is, for example, $C_1$-$C_8$-alkyl, in particular $C_1$-$C_4$-alkyl, such as methyl, ethyl, n-propyl, isopropyl, n-butyl, isobutyl, sec-butyl, tert-butyl, n-pentyl, isopentyl, neopentyl, tert-pentyl, n-hexyl, isohexyl or n-heptyl.

N-(lower alkyl)amino is, for example, N—$C_1$-$C_8$-alkylamino, in particular $C_1$-$C_4$-alkylamino, such as methylamino, ethylamino, propylamino, butylamino, isobutylamino, sec-butylamino or tert-butylamino.

N,N-di(lower alkyl)amino is, for example, N,N-di-$C_1$-$C_4$-alkylamino, such as N,N-dimethylamino, N,N-diethylamino, N,N-dipropylamino, N-methyl-N-ethylamino or N-methyl-N-propylamino.

Optionally N-mono or N,N-di-$C_1$-$C_8$-alkylated carbamoyl-$C_1$-$C_8$-alkyl is, for example, carbamoyl, N-methylcarbamoyl, N-ethylcarbamoyl, N-propylcarbamoyl, N-butylcarbamoyl, N-methylcarbamoyl-$C_1$-$C_8$-alkyl, N-ethylcarbamoyl-$C_1$-$C_8$-alkyl, N-propylcarbamoyl-$C_1$-$C_8$-alkyl, N-butylcarbamoyl-$C_1$-$C_8$-alkyl, N,N-di-$C_1$-$C_4$-alkylamino, such as N,N-dimethyl-carbamoyl-$C_1$-$C_8$-alkyl, N,N-diethylcarbamoyl-$C_1$-$C_8$-alkyl, N,N-dipropylcarbamoyl-$C_1$-$C_8$-alkyl, N-methyl-N-ethylcarbamoyl-$C_1$-$C_8$-alkyl or N-methyl-N-propylcarbamoyl-$C_1$-$C_8$-alkyl, where $C_1$-$C_8$-alkyl is, for example, methyl or ethyl.

N-phenyl-N-(lower alkoxy)(lower alkyl)amino is, for example, N-phenyl-N—($C_1$-$C_4$-alkoxy-$C_1$-$C_4$-alkyl)amino, such as N-phenyl-N-(methoxy-$C_1$-$C_4$-alkyl)amino, N-phenyl-N-(ethoxy-$C_1$-$C_4$-alkyl)amino, N-phenyl-N-(propyloxy-$C_1$-$C_4$-alkyl)amino, N-phenyl-N-(isopropyloxy-$C_1$-$C_4$-alkyl)amino or N-phenyl-N-(butyloxy-$C_1$-$C_4$-alkyl)amino, where $C_1$-$C_4$-alkyl is, for example, methyl, ethyl, propyl or butyl, in particular N-phenyl-N-(ethoxymethyl)amino.

N-phenyl-N-(lower alkyl)amino is, for example, N-phenyl-N—$C_1$-$C_4$-alkylamino, such as N-phenyl-N-methylamino, N-phenyl-N-ethylamino, N-phenyl-N-propylamino, N-phenyl-N-isopropylamino or N-phenyl-N-butylamino, in particular N-phenyl-N-methylamino.

N-phenyl-N-(phenyl(lower alkyl))amino is, for example, N-phenyl-N-(phenyl-$C_1$-$C_4$-alkyl)amino, such as N-phenyl-N-benzylamino, N-phenyl-N-(2-phenylethyl)amino, N-phenyl-N-(3-phenylpropyl)amino or N-phenyl-N-(4-phenylbutyl)amino, in particular N-phenyl-N-(2-phenylethyl)amino.

Phenyl(lower alkanoyl) is, for example, phenyl-$C_1$-$C_4$-alkanoyl, where $C_1$-$C_4$-alkanoyl is, for example, acetyl, in particular phenylacetyl.

Polyhalo(lower alkyl) is, for example, di-, tri- or tetrahalo-$C_1$-$C_4$-alkyl, such as trifluoromethyl.

Pyridyl(lower alkyl) is, for example pyridyl-$C_1$-$C_4$-alkyl, in particular pyrid-2-yl-$C_1$-$C_4$-alkyl, where $C_1$-$C_4$-alkyl is, for example, methyl, in particular pyrid-2-ylmethyl or 2-(pyrid-2-yl)ethyl.

Salts of compounds having salt-forming groups are in particular add addition salts, salts with bases or, in the presence of a plurality of salt-forming groups, in some cases also mixed salts or internal salts. Salts are primarily the pharmaceutically usable or nontoxic salts of compounds of the formula I.

Such salts are formed, for example, from compounds of the formula I with an acidic group, for example a carboxyl or sulpho group, and are, for example, the salts thereof with suitable bases, such as nontoxic metal salts derived from metals of group Ia, Ib, IIa and IIb of the Periodic Table of the Elements, for example alkali metal, in particular lithium, sodium or potassium salts, alkaline earth metal salts, for example magnesium or calcium salts, and also zinc salts or ammonium salts, including those salts which are formed with organic amines, such as optionally hydroxy-substituted mono-, di- or trialkylamines, in particular mono-, di- or tri(lower alkyl)amines, or with quaternary ammonium bases, for example methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy(lower alkyl))amines, such as N,N-dimethyl-N-2-hydroxy-ethyl)amine, or N-methyl-D-glucamine, or quaternary ammonium hydroxides, such as tetra-butylammonium hydroxide. The compounds of the formula I having a basic group, for example an amino group, may form acid addition salts, for example with suitable inorganic acids, e.g. hydrohalic acid such as hydrochloric acid, hydrobromic add, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic, sulpho or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, ditric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the α-amino acids mentioned above, and also methanesulphonic acid, ethanesulphonic acid, 2-hydroxyethanesulphonic acid, ethane-1,2-disulphonic acid, benzenesulphonic acid, 4-methylbenzenesulphonic acid, naphthalene-2-sulphonic acid, 2- or 3-phosphoglycerate, glucose 6-phosphate, N-cyclohexylsulphamic acid (with formation of cyclamates) or with other acidic organic compounds such as ascorbic acid. Compounds of the formula I with acidic and basic groups may also form internal salts.

For the isolation and purification, pharmaceutically unsuitable salts may also find use.

The invention relates, for example, to compounds of the formula I where $R_1$ a) is hydrogen; or is b) $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4 $C_1$-$C_8$-alkyl, halogen, cyano, oxide, oxo, trifluoromethyl, $C_1$-$C_8$-alkoxy, $C_1$-$C_8$-alkoxycarbonyl, aryl or heterocyclyl;

$R_2$ is a) $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_8$-cycloalkyl-$C_1$-$C_8$-alkanoyl, aryl-$C_1$-$C_8$-alkanoyl, aryl-$C_3$-$C_8$-cycloakanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloakoxy, amino, $C_{1-6}$-alkylamino, di-$C_{1-8}$-alkylamino, $C_0$-$C_6$-alkylcarbonylamino, $C_1$-$C_6$-alkoxycarbonylamino, halogen, oxo, cyano, hydroxyl, oxide, trifluoromethyl, $C_1$-$C_8$-alkoxy, optionally N-mono- or N,N-di-$C_1$-$C_8$-alkylated carbamoyl-$C_0$-$C_8$-alkyl, optionally esterified carboxyl, $C_{1-6}$-alkylenedioxy, aryl or heterocyclyl; or is b) together with $R_1$ and the nitrogen atom to which they are bonded, a saturated or partly unsaturated 4-8-membered heterocyclic ring which may contain an additional nitrogen, oxygen or sulphur atom or a —SO— or —SO2- group, in which case the additional nitrogen atom may optionally be substituted by $C_1$-$C_8$-alkyl, $C_1$-$C_8$-alkanoyl, $C_1$-$C_8$-alkoxycarbonyl, aryl or heteroaryl radicals, and this heterocyclic ring may be part of a bicyclic or tricyclic ring system having a total of up to 16 members and the second ring may also contain a nitrogen, oxygen or sulphur atom or a —SO— or —SO2- group, and the nitrogen atom in the second ring may optionally be substituted by $C_1$-$C_8$-alkyl, $C_1$-$C_8$-alkanoyl, $C_1$-$C_8$-alkoxycarbonyl, aryl or heterocyclyl radicals, and all ring systems mentioned may be substituted by 1-4 $C_1$-$C_8$-alkyl, halogen, hydroxyl, cyano, oxide, oxo, trifluoromethyl, $C_1$-$C_8$-alkoxy, $C_1$-$C_8$-alkoxy-$C_1$-$C_8$-alkoxy, $C_1$-$C_8$-alkoxycarbonylamino, $C_0$-$C_8$-alkylcarbonylamino, $C_1$-$C_8$-alkylamino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy or heterocyclyloxy-$C_0$-$C_4$-alkyl-$C_1$-$C_8$-alkoxy;

$R_3$ is hydrogen, $C_1$-$C_8$-alkyl, $C_1$-$C_8$-alkoxycarbonyl or $C_1$-$C_8$-alkanoyl;

$R_4$ is hydrogen, $C_1$-$C_8$-alkyl, $C_1$-$C_8$-alkoxycarbonyl or $C_1$-$C_8$-alkanoyl;

$R_5$ are each independently hydrogen or $C_1$-$C_8$-alkyl, $R_6$ is oxygen,

R is arylamino, N-aryl-N-(lower alkoxy)(lower alkyl))amino, N-aryl-N-aryl(lower alkyl)amino or heterocyclyl bonded via a ring nitrogen atom, in which case the heterocyclyl mentioned, apart from the ring nitrogen atom via which it is bonded, may contain further ring heteroatoms selected from oxygen, nitrogen, nitrogen substituted by lower alkyl, lower alkanoyl, (lower alkane)sulphonyl or (lower alkoxy)carbonyl, sulphur, and sulphur bonded to 1 or 2 oxygen atoms, and salts thereof The invention relates primarily to compounds of the formula I where R is unsubstituted or anilino or naphthylamino which are each unsubstituted or substituted in the phenyl or naphthyl moiety as specified below, N-phenyl- or N-naphthyl-N(lower alkoxy)(lower alkyl)amino which are each unsubstituted or substituted in the phenyl or naphthyl moiety as specified, N-phenyl- or N-naphthyl-N-(lower alkyl)amino which are each unsubstituted or substituted in the phenyl or naphthyl moiety as specified, or 5- to 8-membered heterocyclyl which is bonded via a ring nitrogen atom and is optionally fused with 1 or 2 fused-on phenyl or cycloalkyl radicals, and which may contain 1 or 2 further ring heteroatoms selected from oxygen, nitrogen and optionally oxidized sulphur, where phenyl, naphthyl and phenyl or naphthyl radicals as a constituent of napthylamino, N-phenyl- or N-naphthyl-N-(lower alkoxy)(lower alkyl)amino, N-phenyl- or N-naphthyl-N-(lower alkyl)amino, may be mono- or polysubstituted, for example mono- or disubstituted, by lower alkyl, hydroxy, lower alkoxy, carbamoyl(lower alkoxy), N-(lower alkyl)carbamoyl(lower alkoxy), N-(lower alkyl)carbamoyl, N,N-di(lower alkyl)carbamoyl(lower alkoxy), amino, N-(lower alkyl)- or N,N-di(lower alkyl)amino, carboxy, (lower alkoxy)carbonyl, carbamoyl, sulphamoyl, (lower alkane)sulphonyl, halogen, nitro, phenyl, 5- or 6-membered heteroaryl containing as a heteroatom 1 nitrogen, sulphur or oxygen atom, 2 nitrogen atoms, 1 nitrogen atom and 1 sulphur atom, or 1 nitrogen and 1 oxygen atom, such as pyridyl, and/or by cyano, and R radicals may be N-substituted by lower alkyl, lower alkanoyl, (lower alkoxy)carbonyl, or (lower alkane)sulphonyl, S-mono- or S,S-disubstituted by oxy, and/or mono- or di-C-substituted by lower alkyl, hydroxy(lower alkyl), (lower alkoxy)(lower alkyl), (lower alkenyl)oxy(lower alkyl), naphthoxy(lower alkyl), phenyloxy(lower alkyl), phenyl(lower alkoxy) (lower alkyl), (lower alkanoyl)oxy(lower alkyl), benzoyloxy(lower alkyl), (lower alkoxy)carbonyloxy(lower alkyl), phenyloxycarbonyloxy(lower alkyl), phenyl(lower alkoxy)carbonyloxy(lower alkyl), amino(lower alkyl), N-(lower alkyl)amino(lower alkyl), N,N-di(lower alkyl)amino(lower alkyl), carbamoyl(lower alkyl), (lower alkanoyl)amino(lower alkyl), benzoylamino(lower alkyl), (lower alkoxy)carbonylamino(lower alkyl), (lower alkoxy)carbonyl (lower alkyl), (lower alkoxy)(lower alkoxy)(lower alkyl), (lower alkyl)thio(lower alkoxy)(lower alkyl), N-(lower alkoxy)imino(lower alkyl), cycloalkoxy(lower alkyl), cycloalkyl(lower alkoxy)(lower alkyl), lower alkenyl, (lower alkenyl)oxy, (lower alkoxy)(lower alkenyl), lower-alkynyl, (lower alkynyl)oxy, lower alkanoyl, oxo, hydroxyl, lower alkoxy, carbamoyl(lower alkoxy), N-(lower alkyl)carbamoyl (lower alkoxy), N-(lower alkyl)carbamoyloxy, N,N-di(lower alkyl)carbamoyloxy, (lower alkoxy)(lower alkoxy), (lower alkyl)thio(lower alkoxy), (lower alkanoyl)oxy, benzoyloxy, N-(lower alkylcarbamoyl, amino, N-(lower alkyl)amino, N,N-di(lower alkyl)amino, (lower alkanoyl)amino, benzoylamino, cycloalkylcarbonylamino, cycloalkyl(lower alkanoyl)amino, (lower alkoxy)carbonyl(lower alkyl)amino, (lower alkenyl)oxycarbonylamino, (lower alkoxy)(lower alkoxy)carbonylamino, (lower alkoxy)(lower alkanoyl) amino, N-(lower alkyl)carbamoylamino, N,N-di(lower alkyl) carbamoylamino, N-(lower alkanoyl)N-(lower alkyl)amino, (lower alkoxy)carbonylamino, N-(lower alkoxy)carbonyl-N-(lower alkyl)amino, N,N-(lower alkylene)amino, N,N-(1-oxo(lower alkylene))amino, N,N-(1-oxo-2-oxa(lower alkylene))amino, carboxyl, (lower alkoxy)carbonyl, phenyl(lower alkoxy)carbonyl, phenyloxycarbonyl, pyrrolidinylcarbonyl, piperidinylcarbonyl, piperazinylcarbonyl, morpholinylcarbonyl, thiomorpholinylcarbonyl, S,S-dioxothiomorpholinylcarbonyl, cyano, carbamoyl, N,N-di(lower alkyl)carbamoyl, N-(lower alkenyl)carbamoyl, N-cycloalkylcarbamoyl, N-cycloalkyl(lower alkyl)carbamoyl, N-hydroxy(lower alkyl)carbamoyl, N-(lower alkoxy)(lower alkyl)carbamoyl, N-carboxy(lower alkyl)carbamoyl, carbamoyl(lower alkyl) carbamoyl, (lower alkoxy)carbonyl(lower alkyl)carbamoyl, phenyl, dioxolan-2-yl, oxazol-2-yl, oxazolin-2-yl, oxazolidin-2-yl, nitro, sulphamoyl, (lower alkane)sulphonyl, phosphono, (lower alkane)phosphono, di(lower alkyl) phosphono and/or halogen.

The invention relates in particular to compounds of the formula I where R is an anilino, naphthylamino, N-phenyl-N-($C_1$-$C_4$-alkoxy-$C_1$-$C_4$-alkyl)amino such as N-phenyl-N-(ethoxymethyl)amino, or N-phenyl-N-(phenyl-$C_1$-$C_4$-alkyl) amino such as N-phenyl-N-(2-phenylethyl)amino which are each unsubstituted, or mono- or disubstituted in the phenyl or naphthyl moiety by $C_1$-$C_4$-alkoxy such as methoxy, $C_1$-$C_4$-alkoxycarbonyl such as methoxy-, ethoxy-, isopropyloxy- or tert-butyloxycarbonyl, carbamoyl-$C_1$-$C_4$-alkoxy such as carbamoylmethoxy, $C_1$-$C_4$-alkanoylamino-$C_1$-$C_4$-alkyl such as formylaminomethyl, $C_1$-$C_4$-alkoxycarbonylamino-$C_1$-$C_4$-alkyl such as methoxycarbonylaminomethyl, halogen and/or optionally N-oxidized pyridyl such as pyrid-3-yl or 1-oxidopyrid-3-yl, or is pyrrolidino, piperidino, piperazine, morpholino or thiomorpholino, indolin-1-yl, isoindolin-2-yl, 2,3-dihydrobenzimidazol-1-yl, 1,2,3,4-tetrahydroquinol-1-yl, 1,2,3,4-tetrahydroisoquinol-2-yl, 1,2,3,4-tetrahydro-1,3-benzodiazin-1-yl, 1,2,3,4-tetrahydro-1,4-benzodiazin-1-yl, 3,4-dihydro-2H-1,4-benzoxazin-4-yl, optionally S,S-dioxidized 3,4-dihydro-2H-1,3-benzothiazin-1-yl, 3,4,5,6,7,8-hexahydro-2H-1,4-benzoxazin-4-yl, 3,4,5,6,7,8-hexahydro-2H-1,4-benzothlazin-4-yl, 2,3,4,5-tetrahydro-1H-1-benzo[6,7-b]azepin-1-yl or 5,6-dihydrophenanthridin-5-yl which are each unsubstituted or mono-, di- or trisubstituted by $C_1$-$C_4$-alkyl such as methyl, hydroxy-$C_1$-$C_4$-alkyl such as hydroxymethyl, $C_1$-$C_4$-alkoxy-$C_1$-$C_4$-alkyl such as methoxymethyl or propyloxymethyl, $C_3$-$C_5$-alkenyloxy-$C_1$-$C_4$-alkyl such as allyloxymethyl, $C_1$-$C_4$-alkoxy-$C_1$-$C_4$-alkoxy-$C_1$-$C_4$-alkyl such as methoxymethoxymethyl or 2-methoxyethoxymethyl, $C_1$-$C_4$-alkoxycarbonylamino-$C_1$-$C_4$-alkyl such as methoxy- or ethoxycarbonylaminomethyl, $C_1$-$C_4$-alkoxyimino-$C_1$-$C_4$-alkyl such as methoxyiminomethyl, ethoxylminomethyl or propoxyiminomethyl, carboxyl, $C_1$-$C_4$-alkoxycarbonyl such as methoxy-, ethoxy-, isopropyloxy- or tert-butyloxycarbonyl, cyano, carbamoyl, N—$C_1$-$C_8$-alkylcarbamoyl such as N-methyl- or N-butylcarbamoyl, N,N-di-$C_1$-$C_4$alkylcarbamoyl such as N,N-dimethyl-carbamoyl, $C_1$-$C_4$-alkoxy-$C_1$-$C_4$-alkylcarbamoyl such as N-(2-propyloxyethyl)carbamoyl, N-carboxy-$C_1$-$C_4$-alkylcarbamoyl such as N-carboxymethylcarbamoyl, morpholinocarbonyl, $C_1$-$C_4$-alkoxy such as propyloxy, $C_1$-$C_4$-alkoxy-$C_1$-$C_4$-alkoxy such as methoxymethoxy or 2-methoxyethoxy, $C_1$-$C_4$-alkanoyloxy such as acetoxy or benzoyloxy, $C_1$-$C_4$-alkanoylamino, such as acetylamino, $C_1$-$C_4$-alkoxycarbonylamino such as methoxycarbonylamino, 3- to 6-membered cycloalkylcarbonylamino such as cyclopropylcarbonylamino, N—$C_1$-$C_4$-alkoxy-$C_1$-$C_4$alkanoylamino such as methoxyacetylamino, N—$C_1$-$C_4$-alkylcarbamoylamino such as methylcarbamoylamino, or 5- or 6-membered N,N-(1-oxo(lower alkylene))amino or N,N-(1-oxo-2-oxa(lower-alkylene))amino such as 2-oxopyrrlidin-1-yl or 2-oxooxazolidin-3-yl, $C_1$-$C_8$-alkanoyl such as acetyl, oxo, nitro, $C_1$-$C_4$-alkanesulphonyl such as methane- or ethanesulphonyl, and/or halogen.

The invention relates in particular to compounds of the formula I where R is a group of the formula

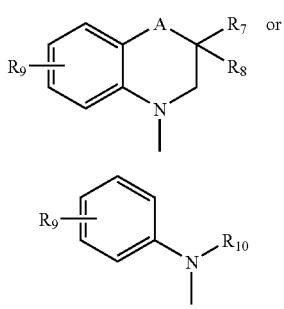

in which

A is a direct bond, methylene, dimethylene, imino, oxy or thio, $R_7$ is $C_1$-$C_4$-alkoxy-$C_1$-$C_4$-alkyl, such as methoxy- or propyloxymethyl, $C_3$-$C_5$-alkenyloxy-$C_1$-$C_4$-alkyl, such as allyloxymethyl, $C_1$-$C_4$-alkoxy-$C_1$-$C_4$-alkoxy-$C_1$-$C_4$-alkyl, such as methoxymethoxymethyl or 2-methoxyethoxymethyl, $C_1$-$C_4$-alkoxycarbonylamino-$C_1$-$C_4$-alkyl, such as methoxy- or ethoxycarbonylaminomethyl, $C_1$-$C_4$-alkoxyimino-$C_1$-$C_4$-alkyl, such as methoxyiminomethyl, phenyl, $C_1$-$C_4$-alkoxycarbonyl, such as methoxycarbonyl, ethoxycarbonyl or isopropyloxycarbonyl, cyano, carbamoyl, N—$C_1$-$C_4$-alkylcarbamoyl, such as N-methylcarbamoyl, N-ethylcarbamoyl or N-butylcarbamoyl, $C_1$-$C_4$-alkoxy-$C_1$-$C_4$-alkylcarbamoyl, such as N-(2-methoxyethyl)carbamoyl, $C_1$-$C_4$-alkoxy such as propyloxy, $C_1$-$C_4$-alkoxy-$C_1$-$C_4$-alkoxy such as methoxymethoxy or 2-methoxyethoxy, $C_1$-$C_8$-alkanoyloxy such as acetoxy, benzoyloxy, N—$C_1$-$C_4$-alkylcarbamoylamino, such as N-methylcarbamoyl-amino, $C_1$-$C_4$-alkanoylamino, such as acetylamino, $C_1$-$C_4$-alkoxycarbonylamino, such as methoxycarbonylamino, 3 to 6-membered cycloalkylcarbonylamino, such as cyclopropylcarbonylamino, $C_1$-$C_4$-alkoxy-$C_1$-$C_4$-alkanoylamino, such as methoxyacetylamino, or 5- or 6-membered N,N-(1-oxo (lower alkylene))amino or N,N-1-oxo-2-oxa(lower alkylene))amino, such as 2-oxopyrrolidin-1-yl or 2-oxooxazolidin-3-yl, N—$C_1$-$C_4$-alkyl-carbamoylamino, such as methylcarbamoylamino, $R_8$ is hydrogen, but may also be $C_1$-$C_4$-alkyl such as methyl, $R_9$ is hydrogen or halogen and $R_{10}$ is $C_1$-$C_4$-alkoxy-$C_1$-$C_4$-alkyl, such as methoxy-$C_1$-$C_4$-alkyl, ethoxy-$C_1$-$C_4$-alkyl, propyloxy-$C_1$-$C_4$-alkyl, isopropyloxy-$C_1$-$C_4$-alkyl, butyloxy-$C_1$-$C_4$-alkyl, isobutyloxy-$C_1$-$C_4$-alkyl, sec-butyloxy-$C_1$-$C_4$-alkyl or tert-butyloxy-$C_1$-$C_4$-alkyl, where $C_1$-$C_4$-alkyl is, for example, ethyl, propyl or butyl, and is in particular 3-methoxypropyl.

Particularly effective in each case are those compounds of the formula I with the stereochemistry (in each case "S") of the main chain shown in the formula

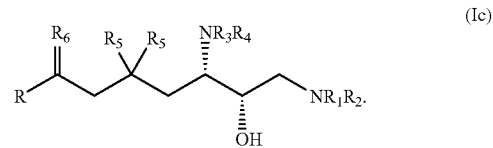

The invention relates in each case preferentially to the stereoisomers of compounds of the formula I with the stereochemistry of the main chain shown in the formula Ic, where the variables are each defined as follows, and salts thereof, in particular pharmaceutically usable salts thereof.

The invention relates specifically to the compounds of the formula I specified in the examples and to salts thereof, in particular to pharmaceutically usable salts thereof.

The invention relates primarily to compounds of the formula

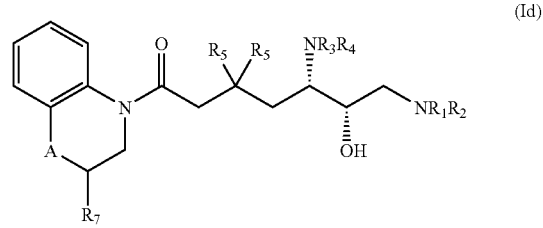

where

A is methylene, oxy or thio, $R_1$ is a) hydrogen; or
is b) $C_1$-$C_8$-alkyl or $C_3$-$C_8$-cycloalkyl;

$R_2$ is a) $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_3$-$C_8$-cycloalkyl, $C_3$-$C_8$-cycloalkoxy, $C_{1-6}$alkylamino, cyano, halogen, hydroxyl, oxide, $C_0$-$C_6$-alkylcarbonylamino, $C_1$-$C_8$-alkoxy, oxo, trifluoromethyl or aryl; or b) together with $R_1$ and the nitrogen atom to which they are bonded, is a saturated or partly unsaturated, 4-8-membered heterocyclic ring which may contain an additional nitrogen or oxygen atom, in which case the additional nitrogen atom may optionally be substituted by $C_1$-$C_8$-alkyl or $C_1$-$C_8$-alkanoyl, and this heterocyclic ring may be part of a bicyclic or tricyclic ring system having a total of up to 16 members, and the second ring may also contain a nitrogen or oxygen atom, in which case the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, cyano, oxide, oxo, $C_1$-$C_8$-alkoxy, $C_1$-$C_8$-alkoxy-$C_1$-$C_8$-alkoxy, $C_1$-$C_8$-alkylcarbonylamino, $C_1$-$C_8$-alkoxycarbonylamino or aryloxy-$C_0$-$C_4$-alkyl-$C_1$-$C_8$-alkoxy;

$R_3$ is hydrogen or —(C═O)—$C_1$-$C_4$-alkyl;

$R_4$ is hydrogen;

$R_5$ are each independently $C_1$-$C_4$-alkyl, such as methyl, $R_7$ is $C_1$-$C_4$-alkoxycarbonylamino such as methoxycarbonylamino, ethoxycarbonylamino, propyloxycarbonylamino, isopropyloxycarbonylamino or butyloxycarbonylamino, $C_1$-$C_4$-alkoxy-$C_1$-$C_4$-alkoxy-$C_1$-$C_4$-alkyl, such as methoxy-$C_1$-$C_4$-alkoxy-$C_1$-$C_4$-alkyl, ethoxy-$C_1$-$C_4$-alkoxy-$C_1$-$C_4$-alkyl, propyloxy-$C_1$-$C_4$-alkoxy-$C_1$-$C_4$-alkyl, isopropyloxy $C_1$-$C_4$-alkoxy-$C_1$-$C_4$-alkyl or butyloxy-$C_1$-$C_4$-alkoxy-$C_1$-$C_4$-alkyl, where $C_1$-$C_4$-alkoxy is, for example, methoxy, ethoxy, propyloxy or butyloxy, and $C_1$-$C_4$-alkyl is, for example, methyl, ethyl, propyl or butyl, in particular methoxymethoxymethyl, 2-methoxyethoxymethyl or 3-methoxypropyloxymethyl, $C_1$-$C_4$-alkoxy-$C_1$-$C_4$-alkyl, such as methoxy-$C_1$-$C_4$-alkyl, ethoxy-$C_1$-$C_4$-alkyl, propyloxy-$C_1$-$C_4$-alkyl, isopropyloxy-$C_1$-$C_4$-alkyl, butyloxy-$C_1$-$C_4$-alkyl, isobutyloxy-$C_1$-$C_4$-alkyl, sec-butyloxy-$C_1$-$C_4$-alkyl or tert-butyloxy-$C_1$-$C_4$-alkyl, where $C_1$-$C_4$-alkyl is, for example, methyl, ethyl, propyl or butyl, in particular ethoxymethyl or 2-methoxyethyl, or N—$C_1$-$C_4$-alkylcarbamoyl, such as N-methylcarbamoyl, N-ethylcarbamoyl, N-propylcarbamoyl or N-butylcarbamoyl, and salts thereof, in particular the pharmaceutically usable salts thereof.

The compounds of the formula (I) may be prepared in an analogous manner to preparation processes known from the literature. The starting materials for carrying out the preparation processes are described, for example, in EP 0702004. The inventive compounds of the formula (I) and salts of such compounds having at least one salt-forming group are obtained by processes known per se, for example by a) condensing a compound of the formula II

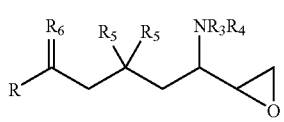

where R, $R_3$, $R_4$, $R_5$ and $R_6$ are each as defined above, or a salt thereof, with a compound of the formula $R_1R_2NH$ (III) where $R_1$ and $R_2$ are each as defined above, in the course of which free functional groups present in the reaction components with the exception of the groups taking part in the reaction are present in protected form, and protecting groups present are detached. In cases where $R_1$ and $R_2$ are a saturated or partly unsaturated oxo-substituted heterocyclic ring (for example lactams) and strong bases are used as a reagent, the alkoxide formed by epoxide opening can react with one of the protecting groups present (for example N-Boc) and form an oxazolidinone which can be cleaved to give the product, for example, with lithium hydroxide, or b) condensing a compound of the formula II

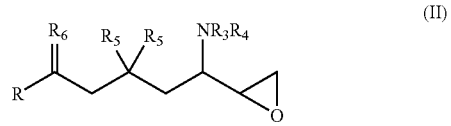

where R, $R_3$, $R_4$, $R_5$ and $R_6$ are each as defined above, or a salt thereof, with an azide, reducing the azido group to amino and then, depending upon the definitions of $R_1$ and $R_2$ mono- or dialkylating, mono- or diacylating, and optionally sulphonylating the amino group, in the course of which free functional groups present in the reaction components with the exception of the groups taking part in the reaction are present in protected form, and detaching protecting groups present, or c) condensing a compound of the formula IV

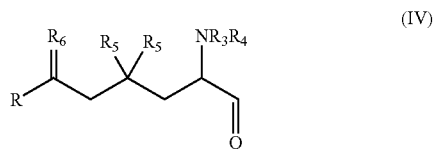

where R, $R_3$, $R_4$, $R_5$ and $R_6$ are each as defined above, or a salt thereof, with cyanide or nitromethane, reducing the nitrile group or nitro group to amino and then, depending upon the definitions of $R_1$ and $R_2$, mono- or dialkylating, mono- or diacylating, and optionally sulphonylating the amino group, in the course of which free functional groups present in the reaction components with the exception of the groups taking part in the reaction are present in protected from, and detaching protecting groups present.

Compounds of the formula II can be prepared in an analogous manner to preparation processes known from the literature, for example by a) condensing a compound of the formula IV

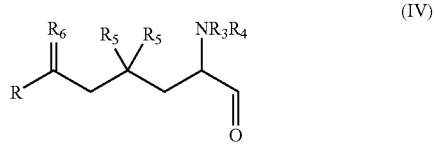

where R, $R_3$, $R_4$, $R_5$ and $R_6$ are each as defined above, or a salt thereof, with methylide (see, for example, in Tet. Lett. 30(40), 5425-5428, 1989), in the course of which free functional groups present in the reaction components with the exception of the groups taking part in the reaction are present in protected form, and detaching protecting groups present, or b) epoxidizing a compound of the formula V

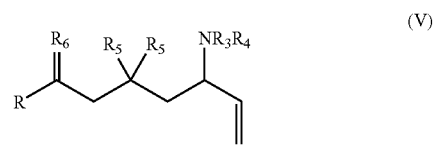

where R, $R_3$, $R_4$, $R_5$ and $R_6$ are each as defined above, or a salt thereof, (see, for example, in J. Med. Chem. 35(10), 1685-1701, 1992 and J. Org. Chem. 59(3), 653657, 1994), in the course of which free functional groups present in the reaction components with the exception of the groups taking part in the reaction are present in protected form, and detaching protecting groups present, or c) dihydroxylating a compound of the formula V

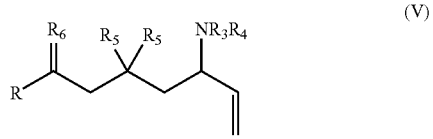

where R, $R_3$, $R_4$, $R_5$ and $R_6$ are each as defined above, or a salt thereof, tosylating the primary alcohol and subsequently admixing it with a base such as potassium hydroxide (see, for example, in WO 03050073), in the course of which free functional groups present in the reaction components with the exception of the groups taking part in the reaction are present in protected form, and detaching protecting groups present, or d) preparing an activated ester from a compound of the formula VI

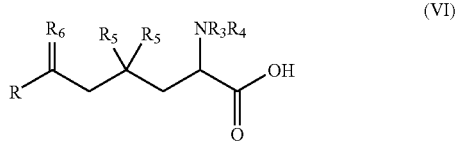

where R, $R_3$, $R_4$, $R_5$ and $R_6$ are each as defined above, or a salt thereof, and admixing it with diazomethane, admixing the diazoketone with 48% HBr, and then reducing the bromoketone, and subsequently admixing it with a base such as potassium hydroxide (see, for example, in WO 03050073), in the course of which free functional groups present in the reaction components with the exception of the groups taking part in the reaction are present in protected form, and detaching protecting groups present.

Details of the specific preparation variants can be taken from the examples.

The compounds of the formula (I) may also be prepared in optically pure form. The separation into antipodes may be effected by methods known per se, either preferably at a synthetically early stage by salt formation with an optically active acid, for example (+)- or (−)-mandelic acid and separation of the diastereomeric salts by fractional crystallization, or preferably at a rather later stage by derivatization with a chiral auxiliary building block, for example (+)- or (−)-camphanoyl chloride, and separation of the diastereomeric products by chromatography and/or crystallization and subsequent cleavage of the bond to the chiral auxiliary. To determine the absolute configuration of the piperidine present, the pure diastereomeric salts and derivatives may be analysed with common spectroscopic methods, of which X-ray spectroscopy on single crystals constitutes a particularly suitable method.

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically usable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-(amino, mono- or dialkylamino, carboxyl, lower alkoxycarbonyl)-alkyl esters or such as lower α-(alkanoyloxy, alkoxycarbonyl or dialkylaminocarbonyl)-alkyl esters; as such, pivaloyloxymethyl esters and similar esters are utilized in a conventional manner.

Owing to the dose relationship between a free compound, a prodrug derivative and a salt compound, a certain compound in this invention also encompasses its prodrug derivative and salt form, where this is possible and appropriate.

The compounds of the formula (I) also include those compounds in which one or more atoms are replaced by their stable, non-radioactive isotopes; for example, a hydrogen atom by deuterium.

The compounds of the formula (I) and the pharmaceutically usable salts thereof have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the release of the hormone aldosterone which inhibits the release of the sodium ion from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

The action of renin inhibitors is detected experimentally with an in vitro test [Nussberger et al. (1987) J. Cardiovascular Pharmacol., Vol. 9, p. 39-44]. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-6}$ to about $10^{-10}$ mol/l.

In salt-depleted animals, renin inhibitors bring about a blood pressure decrease. Human renin differs from renin of other species. To test inhibitors of human renin, primates (marmosets, Callithrixjacchus) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulphonyl)-4-chloro-2-[(2-furanylmethyl)amino]benzoic acid) (5 mg/kg). 16 hours after the injection of furosemide, the test substances are administered either directly into the femoral artery by means of an injection cannula or into the stomach by gavage as a suspension or solution, and their effect on blood pressure and heart rate is evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the formula (I) and the pharmaceutically usable salts thereof may find use as medicines, for example in the form of pharmaceutical preparations. The pharmaceutical preparations may be administered enterally, such as orally, for example in the form of tablets, coated tablets, sugar-coated tablets, hard and soft gelatine capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatine capsules, the compounds of the formula (I) and pharmaceutically usable salts thereof may be processed with pharmaceutically inert, inorganic or organic excipients. Such excipients used, for example for tablets, coated tablets and hard gelatine capsules, may be lactose, corn starch, or derivatives thereof, talc, stearic acid or salts thereof etc.

Suitable excipients for soft gelatine capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile acids, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other the therapeutically valuable substances.

The present invention further provides the use of the compounds of the formula (I) and the pharmaceutically usable salts thereof in the treatment or prevention of hypertension and heart failure, and also glaucoma, cardiac infarction, kidney failure and restenoses.

The compounds of the formula (I) and the pharmaceutically usable salts thereof may also be administered in combination with one or more agents having cardiovascular action, for example α- and β-blockers such as phentolamine, phenoxybenzamine, prozosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide, indacrinone, metolazone, spironolactone, triamteren, chlorthalidone etc.; sympatholytics such as methyldopa, donidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formula (I) are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

The examples which follow illustrate the present invention. All temperatures are reported in degrees Celsius, pressures in mbar. Unless stated otherwise, the reactions take place at room temperature. The abbreviation "Rf=xx (A)" means, for example, that the Rf value xx is obtained in the solvent system A. The ratio of the solvents relative to one another is always reported in parts by volume. Chemical names of end products and intermediates were obtained with the aid of the program AutoNom 2000 (Automatic Nomenclature).

HPLC gradients on Hypersil BDS C-18 (5 µm); column: 4×125 mm

I 90% water*/10% acetonitrile* to 0% water*/100% acetonitrile* in 5 minutes+2.5 minutes (1.5 ml/min)

II 95% water*/15% acetonitrile* to 0% water*/100% acetonitrile* in 40 minutes (0.8 ml/min)

*: containing 0.1% trifluoroacetic acid

The following abbreviations are used:

Rf ratio of the distance which a substance travels to the distance of the eluent front from the starting point in thin layer chromatography Rt retention time of a substance in HPLC (in minutes)

m.p. melting point (temperature)

General Method A: (N-BOC Deprotection)

A solution of 0.2 mmol of "N-BOC derivative" in 2 ml of 4N HCl (in dioxane) is stirred for 2-6 hours at 0° C. The mixture is concentrated and tert-butanol is added to the residue. The title compound is obtained from the residue by lyophilization.

EXAMPLE 1

[1-(5(S)-Amino-6(S-hydroxy-3,3-dimethyl-7-piperidin-1-yl-heptanoyl)-1,2,3,4-tetrahydro-quinolin-3(R,S)-yl]-carbamic acid methyl ester dihydrochloride

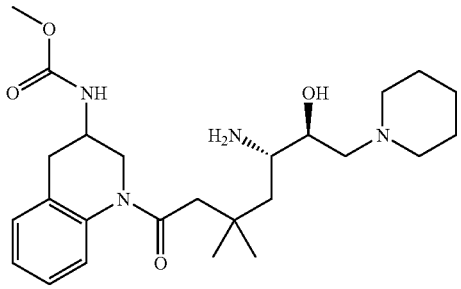

Analogously to Method A, 0.040 g of [1-(5(S)-tert-butoxycarbonylamino-6(S)-hydroxy-3,3-dimethyl-7-piperidin-1-yl-heptanoyl)-1,2,3,4-tetrahydro-quinolin-3(R,S)-yl]-carbamic acid methyl ester are used to prepare the title compound which is obtained as a white solid. Rf=0.18 (200:40:1 dichloromethane-methanol-25% conc. ammonia); Rt=2.82 (gradient I).

The starting materials are prepared as follows:

a) [1-(5(S)-tert-Butoxycarbonylamino-6(S-hydroxy-3,3-dimethyl-7-piperidin-1-yl-heptanoyl)-1,2,3,4-tetrahydro-quinolin-3(R,S)-yl]-carbamic acid methyl ester A solution of 0.030 g of [1-(5(S)-tert-butoxycarbonylamino-3,3-dimethyl-5-(R)-oxiranyl-pentanoyl)-1,2,3,4-tetrahydro-quinolin-3(R,S)-yl]-carbamic acid methyl ester and 0.05 ml piperidine in 0.6 ml of isopropanol is stirred at 70° C. for 1 hour, then cooled to room temperature and concentrated. The title compound is obtained as a beige oil from the residue by means of flash chromatography (SiO2 60 F). Rt=3.89 (gradient I).

b) [1-(5(S)-tert-Butoxycarbonylamino-3,3-dimethyl-5-(R)-oxiranyl-pentanoyl)-1,2,3,4-tetrahydro-quinolin-3(R,S)-yl]-carbamic acid methyl ester 8.69 g of magnesium monoperoxyphthalate hexahydrate are added to a solution of 1.69 g of [1-(5(S)-tert-butoxycarbonylamino-3,3-dimethyl-hept-6-enoyl)-1,2,3,4-tetrahydro-quinolin-3(R,S)-yl]-carbamic acid methyl ester in 30 ml of methanol under argon at room temperature and the mixture is stirred at room temperature for 4 days. The mixture is poured into a mixture of ice and saturated aqueous sodium bicarbonate solution and extracted with tert-butyl methyl ether (2×). The combined organic layers are washed with water and brine, dried over sodium sulphate, filtered and concentrated. The title compound is obtained as a white solid from the residue by means of flash chromatography (SiO2 60 F). Rf=0.5 (3:2 EtOAc-heptane); Rt=4.34 (gradient I).

c) [1-(5(S)-tert-Butoxycarbonylamino-3,3-dimethyl-hept-6-enoyl)-1,2,3,4-tetrahydro-quinolin-3(R,S)-yl]-carbamic acid methyl ester 4.60 g of methyltriphenylphosphonium bromide are added to a solution of 2.70 g of solid potassium bis(trimethylsilyl)amide in 60 ml of diethyl ether under argon at 0° and the mixture is stirred 30 minutes at 0° C. A solution of 1.98 g of [1-(5(S)-tert-butoxycarbonylamino-3,3-dimethyl-oxo-hexanoyl)-1,2,3,4-tetrahydro-quinolin-3(R,S)-yl]-carbamic acid methyl ester in 20 ml of diethyl ether is added dropwise at 0° C. The mixture is stirred at 0° C. for 1 hour, then poured into saturated aqueous ammonium chloride solution and extracted with tert-butyl methyl ether (2×). The combined organic layers are washed with water and brine, dried over sodium sulphate, filtered and concentrated. The title compound is obtained as a white solid from the residue by means of flash chromatography (SiO2 60 F). Rf=0.28 (1:1 EtoAc-heptane); Rt=4.79 (gradient I).

d) [1-(5(S)-tert-butoxycarbonylamino-3,3-dimethyl-6-oxo-hexanoyl)-1,2,3,4-tetrahydro-quinolin-3(R,S)-yl]-carbamic acid methyl ester 2.10 ml of triethylamine are added to a solution of 2.34 g of [1-(5(S)-tert-butoxycarbonylamino-6-hydroxy-3,3-dimethyl-hexanoyl)-1,2,3,4-tetrahydro-quinolin-3(R,S)-yl]-carbamic acid methyl ester in 20 ml of methylene chloride under argon at 0° C. The mixture is stirred for 5 minutes at 0° C. and then a solution of 2.65 g of pyridine sulfur trioxide in 12 ml of dimethylsulfoxide is added dropwise at 0-5° C. over 1 hour. The mixture is stirred at 0-5° C. for 30 minutes and then ice water is added dropwise to the mixture at 0-10° C. The mixture is stirred at 10° C. for 10 minutes and then extracted with methylene chloride (3×). The combined organic layers are washed successively with 10% aqueous sodium hydrogensulfate solution, water, 10% aqueous sodium bicarbonate solution and brine, dried over sodium sulphate, filtered and concentrated. The title compound is obtained as a white solid. Rf=0.44 (3:1 EtOAc-heptane); Rt=4.17 (gradient I).

e) [1-(5(S)-tert-Butoxycarbonylamino-6-hydroxy-3,3-dimethyl-hexanoyl)-1,2,3,4-tetrahydro-quinolin-3-yl]-carbamic acid methyl ester A solution of 3.1 g of 4(S)-[4-(3(R,S)-methoxycarbonylamino-3,4-dihydro-2H-quinolin-1-yl)-2,2-dimethyl-4-oxo-butyl]-2,2-dimethyl-oxazolidine-3-carboxylic acid tert-butyl ester and 104 mg of p-toluenesulfonic acid monohydrate in 49 ml of methylene chloride under argon is stirred at room temperature for 3.5 hours. More p-toluenesulfonic acid monohydrate (200 mg) is added and the mixture is stirred at room temperature for 1.5 hours The solution is concentrated. The title compound is obtained as a white solid from the residue by means of flash chromatography (SiO2 60 F). Rf=0.14 (3:1 EtOAc-heptane); Rt=3.91 (gradient I).

f) 4(S)-[4-(3(R,S)-Methoxycarbonylamino-3,4-dihydro-2H-quinolin-1-yl)-2,2-dimethyl-4-oxo-butyl]-2,2-dimethyl-oxazolidine-3-carboxylic acid tert-butyl ester 8.88 ml of triethylamine are added to a solution of 6.67 g of 4(S)-(3-carboxy-2,2-dimethyl-propyl)-2,2-dimethyl-oxazolidine-3-carboxylic acid tert-butyl ester in 200 ml of methylene chloride under argon. The mixture is cooled to 15° C. and 5.54 g of bis(2-oxo-3-oxazolidinyl)phosphinic chloride are added. The mixture is stirred at room temperature for 2 hours. A solution of 4.36 g of (1,2,3,4-tetrahydro-quinolin-3(R,S)-yl)-carbamic acid methyl ester [177202-73-2] in 100 ml of methylene chloride is added, followed by addition of 2.11 g of 4-N,N-dimethylaminopyridine. The reaction mixture is stirred at room temperature for 17 hours. The mixture is poured into 1M NaOH and extracted with tert-butyl methyl ether (2×). The combined organic layers are washed with water and brine, dried over sodium sulphate, filtered and concentrated. The title compound is obtained as a slightly yellow oil from the residue by means of flash chromatography (SiO2 60 F). Rf=0.39 (1:3 EtOAc-heptane); Rt=5.03 (gradient I).

g) 4(S)-(3-Carboxy-2,2-dimethyl-propyl)-2,2-dimethyl-oxazolidine-3-carboxylic add tert-butyl ester 647 mg of lithium hydroxide monohydrate are added to a solution of 1.13 g of 4(S)-(3-ethoxycarbonyl-2,2-dimethyl-propyl)-2,2-dimethyl-oxazolidine-3-carboxylic acid tert-butyl ester in 50 ml of tetrahydrofuran, 50 ml of methanol and 50 ml of water. The mixture is stirred at room temperature for 16.5 hours and concentrated. Water and ethyl acetate are added to the mixture. The layers are separated and the aqueous layer is extracted with ethyl acetate (2×). The aqueous layer is acidified to pH 3 with 4M HCl and extracted with ethyl acetate (3×). The combined organic layers from the second extraction are dried over sodium sulphate, filtered and concentrated. The title compound is obtained as a colourless oil from the residue by means of flash chromatography (SiO2 60 F). Rf=0.29 (1:1 EtOAc-heptane+1% AcOH); Rt=4.31 (gradient I).

h) 4(S)-(3-Ethoxycarbonyl-2,2-dimethyl-propyl)-2,2-dimethyl-oxazolidine-3-carboxylic acid tert-butyl ester 2.23 g of silver oxide are added to a solution of 3.58 g of 4(S)-(4-diazo-2,2-dimethyl-3-oxo-butyl)-2,2-dimethyl-oxazolidine-3-carboxylic acid tert-butyl ester in 150 ml of absolute ethanol under argon. The mixture is stirred at 50° C. for 5 hours. The mixture is filtered over Hyflo® and concentrated. The title compound is obtained as a colourless oil from the residue by means of flash chromatography (SiO2 60 F). Rf=0.38 (1:3 EtOAc-heptane); Rt=5.49 (gradient I).

i) 4(S)-(4-Diazo-2,2-dimethyl-3-oxo-butyl)-2,2-dimethyl-oxazolidine-3-carboxylic acid tert-butyl ester To a solution of 5.43 g of (S)-4-(2-carboxy-2-methyl-propyl)-2,2-dimethyl-oxazolidine-3-carboxylic add tert-butyl ester in 160 ml of methylene chloride under argon is successively added 2.19 ml of pyridine, 0.1 ml of N,N-dimethylformamide and 3.18 ml of oxalyl chloride. The mixture is stirred at room temperature for 1.5 hours, and then 550 ml of diazomethane solution (0.02 M in ether) are added dropwise. The mixture is concentrated. The title compound is obtained as a yellow oil from the residue by means of flash chromatography (SiO2 60 F). Rf=0.37 (1:3 EtOAc-heptane); Rt=4.65 (gradient I).

j) 4(S)-(2-Carboxy-2-methyl-propyl)-2,2-dimethyl-oxazolidine-3-carboxylic acid tert-butyl ester A mixture of 9.48 g of 4(S)-(2-benzyloxycarbonyl-2-methyl-propyl)-2,2-dimethyl-oxazolidine-3-carboxylic acid tert-butyl ester and 2.58 g of 10% Pd/C in 100 ml of ethyl acetate is hydrogenated at room temperature for 4.5 hours. The solid is removed by filtration over Hyflo®. The mixture is concentrated and re-dissolved in ethyl acetate and 2N NaOH. The layers are separated and the aqueous layer is extracted with ethyl acetate (2×). The aqueous layer is acidified to pH 3 with 4M HCl and extracted with ethyl acetate (3×). The combined organic layers from the second extraction are dried over sodium sulphate, filtered and concentrated. The crude title compound is obtained as a colourless oil. Rf=0.43 (EtOAc-heptane 1:1); Rt=4.23 (gradient I).

k) 4(S)-(2-Benzyloxycarbonyl-2-methyl-propyl)-2,2-dimethyl-oxazolidine-3-carboxylic acid tert-butyl ester To a solution of 247.3 ml of lithium bis(trimethylsilyl)amide (1M in tetrahydrofuran) in 100 ml of tetrahydrofuran at −78° C. is added 15.55 ml of methyl iodide. The mixture is stirred at −78° C. for 10 minutes. A solution of 33.28 g of 4(S)-(2-benzyloxycarbonyl-ethyl)-2,2-dimethyl-oxazolidine-3-carboxylic acid tert-butyl ester in 100 ml of tetrahydrofuran is added dropwise to the mixture at −78° C. The mixture is stirred at −78° C. for 15 minutes, and at 0° C. for 45 minutes. Saturated ammonium chloride solution is added dropwise to the mixture, followed by water. The mixture is extracted with tert-butyl methyl ether (2×). The combined organic layers are dried over sodium sulphate, filtered and concentrated. The title compound is obtained as a yellow oil from the residue by means of flash chromatography (SiO2 60 F). Rf=0.24 (1:5 EtOAc-heptane); Rt=5.83 (gradient I).

l) 4(S)-(2-Benzyloxycarbonyl-ethyl)-2,2-dimethyl-oxazolidine-3-carboxylic acid tert-butyl ester To a solution of 52.46 g of 4(S)-tert-butoxycarbonylamino-5-hydroxy-pentanoic acid benzyl ester [9069-62-8] and 895 mg of p-toluenesulfonic acid hydrate in 125 ml of methylene chloride at 0° C. under argon are added 31 ml of methoxypropene over 15 minutes. The mixture is stirred at 0° C. for 3 hours, then at room temperature for 9 hours. The mixture is washed with saturated sodium bicarbonate solution and dried over sodium sulphate, filtered and concentrated. The title compound is obtained as a yellow oil from the residue by means of flash chromatography (SiO2 60 F). Rf=0.32 (1:3 EtOAc-heptane); Rt=5.32 (gradient I).

Alternative Method (I) for the Synthesis of Compound 1g:

To a solution of 870 mg of 4(S)-(3-cyano-2,2-dimethyl-propyl)-2,2-dimethyl-oxazolidine-3-carboxylic acid tert-butyl ester and 597 mg of potassium hydroxide in 6.68 ml of ethylene glycol is added 0.1 ml of water. The mixture is heated to 200° C. for 8 hours. The mixture is cooled to room temperature and then diluted with water and ethyl acetate. The layers are separated and the aqueous layer is extracted with ethyl acetate (2×). The aqueous layer is acidified to pH 3 with 4M HCl and extracted with ethyl acetate (3×). The combined organic layers from the second extraction are dried over sodium sulphate, filtered and concentrated. The title compound is obtained as a colourless oil from the residue by means of flash chromatography (SiO2 60 F). Rf=0.29 (1:1 EtOAc-heptane+1% AcOH); Rt=4.31 (gradient I).

The starting materials are prepared as follows:

m) 4(S)-(3-Cyano-2,2-dimethyl-propyl)-2,2-dimethyl-oxazolidine-3-carboxylic acid tert-butyl ester A mixture of 2.04 g of 4(S)-(3-methanesulfonyloxy-2,2-dimethyl-propyl)-2,2-dimethyl-oxazolidine-3-carboxylic acid tert-butyl ester and 2.17 g of sodium cyanide in 12 ml of dimethylsulfoxide is heated to 135° C. for 15 hours. The mixture is cooled to room temperature and diluted with water and ethyl acetate. The layers are separated and the aqueous layer is extracted with ethyl acetate. The combined organic layers are dried over sodium sulphate, filtered and concentrated. The title compound is obtained as a colourless oil from the residue by means of flash chromatography (SiO2 60 F). Rf=0.32 (1:1 EtOAc-heptane); Rt=4.82 (gradient I).

n) 4(S)-(3-Methanesulfonyloxy-2,2-dimethyl-propyl)-2,2-dimethyl-oxazolidine-3-carboxylic acid tert-butyl ester To a solution of 1.55 g of 4(S)-(3-hydroxy-2,2-dimethyl-propyl)-2,2-dimethyl-oxazolidine-3-carboxylic acid tert-butyl ester [177198-40-2] in 22 ml of methylene chloride at room temperature under argon is added 3.49 ml of triethylamine and 0.855 ml of methanesulfonyl chloride. The mixture is stirred at room temperature for 13 hours. The reaction is quenched by addition of 35 ml of 0.5M HCl. The mixture is extracted with methylene chloride. The organic layer is concentrated, dried over sodium sulphate and concentrated. The crude title compound is obtained as an orange oil. Rf=0.52 (1:1 EtOAc-heptane); Rt=3.64 (gradient I).

Alternative Method (II) for the Synthesis of Compound 1g:

To a solution of 8.62 4(S)-(4-hydroxy-2,2-dimethyl-butyl-2,2-dimethyl-oxazolidine-3-carboxylic acid tert-butyl ester [177198-37-7] in 193 ml of acetonitrile and 193 ml of carbon tetrachloride is added a solution of 37.4 of sodium periodate and 645 mg of ruthenium trichloride monohydrate in 374 ml of water. The biphasic mixture is rigorously stirred at room temperature for 6 hours. The layers are separated and the aqueous layer is extracted with methylene chloride (2×). The combined organic layers are dried over sodium sulphate, filtered and concentrated. The title compound is obtained as a colourless oil from the residue by means of flash chromatography (SiO2 60 F). Rf=0.29 (1:1 EtOAc-heptane+1% AcOH); Rt=4.31 (gradient I).

According to the processes described in Example 1, the following compounds are prepared in an analogous manner:

| Examples: | |
|---|---|
| 2 | 1-(5(S)-Amino-6(S)-hydroxy-3,3-dimethyl-7-morpholin-4-yl-heptanoyl)-1,2,3,4-tetrahydro-quinolin-3(R;S)-yl]-carbamic acid methyl ester dihydrochloride |
| 3 | {-[5(S)-Amino-7-(9-aza-bicyclo[3.3.1]non-9-yl)-6(S)-hydroxy-3,3-dimethyl-heptanoyl]-1,2,3,4-tetrahydro-quinolin-3(R.S)-yl}-carbamic acid methyl ester dihydrochloride |
| 4 | {1-[5(S)-Amino-7-(cis-2,6-dimethyl-piperidin-1-yl)-6(S)-hydroxy-3,3-dimethyl-heptanoyl}-1,2,3,4-tetrahydro-quinolin-3(R,S)-yl}-carbamic acid methyl ester dihydrochloride |
| 5 | {1-[5(S)-Amino-6(S)-hydroxy-3,3-dimethyl-7-(3(R,S)-methyl-piperidin-1-yl)-heptanoyl]-1,2,3,4-tetrahydro-quinolin-3(R,S)-yl}-carbamic acid methyl ester dihydrochloride |
| 6 | {1-5(S)-Amino-6(S)-hydroxy-3,3-dimethyl-7-(4-methyl-piperidin-1-yl)-heptanoyl]-1,2,3,4-tetrahydro-quinolin-3(R,S)-yl}-carbamic acid methyl ester dihydrochloride |
| 7 | [1-(5(S)-Amino-7-(S)-sec-butylamino-6(S)-hydroxy-3,3-dimethyl-heptanoyl)-1,2,3,4-tetrahydro-quinolin-3(R,S)-yl]-carbamic acid methyl ester dihydrochloride |
| 8 | [1-(5(S)-Amino-7-tert-butylamino-6(S)-hydroxy-3,3-dimethyl-heptanoyl)-1,2,3,4-tetrahydro-quinolin-3(R,S)-yl]-carbamic acid methyl ester dihydrochloride |
| 9 | [-(5(S)-Amino-6(hydroxy-7-isopropylamino-3,3-dimethyl-heptanoyl)-1,2,3,4-tetrahydro-quinolin-3(R,S)-yl]-carbamic acid methyl ester dihydrochloride |
| 10 | [1-(5(S)-Amino-7-(R)sec-butylamino-6(S)-hydroxy-3,3-dimethyl-heptanoyl)-1,2,3,4-tetrahydro-quinolin-3(R,S)-yl]-carbamic acid methyl ester dihydrochloride |
| 11 | {1-[5(S)-Amino-7-(cyclopropylmethyl-amino)-6(S)-hydroxy-3,3-dimethyl-heptanoyl]-1,2,3,4-tetrahydro-quinolin-3(R,S)-yl}-carbamic acid methyl ester dihydrochloride |
| 12 | [1-(5(S)-Amino-7-cyclopentylamino-6(S)-hydroxy-3,3-dimethyl-heptanoyl)-1,2,3,4-tetrahydro-quinolin-3(R,S)-yl]-carbamic acid methyl ester dihydrochloride |
| 13 | [1-(5(S)-Amino-7-benzylamino-6(S)-hydroxy-3,3-dimethyl-heptanoyl)-1,2,3,4-tetrahydro-quinolin-3(R,S)-yl]-carbamic acid methyl ester dihydrochloride |
| 14 | {1-[5(S)-Amino-6(S)-hydroxy-7-(2(R)-methoxymethyl-pyrrolidin-1-yl)-3,3-dimethyl-heptanoyl]-1,2,3,4-tetrahydro-quinolin-3(R,S)-yl}-carbamic acid methyl ester dihydrochloride |
| 15 | {1-[5(S)-Amino-7-(1-carbamoyl-ethylamino)-6(S)-hydroxy-3,3-dimethyl-heptanoyl]-1,2,3,4-tetrahydro-quinolin-3(R,S)-yl}-carbamic acid methyl ester dihydrochloride |
| 16 | {1-[7-(3-Acetylamino-pyrrolidin-1-yl)-5(S)-Amino-6(S)-hydroxy-3,3-dimethyl-heptanoyl]-1,2,3,4-tetrahydro-quinolin-3(R,S)-yl}-carbamic acid methyl ester dihydrochloride |
| 17 | [1-(5(S)-Amino-7-diethylamino-6(S)-hydroxy-3,3-dimethyl-heptanoyl)-1,2,3,4-tetrahydro-quinolin-3(R,S)-yl]-carbamic acid methyl ester dihydrochloride |

EXAMPLE 18

{1-[5(S)-Amino-7-(2,2-dimethyl-propionylamino)-6 (S)-hydroxy-3,3-dimethyl-heptanoyl]-1,2,3,4-tetrahydro-quinolin-3(R,S)-yl}-carbamic acid methyl ester hydrochloride

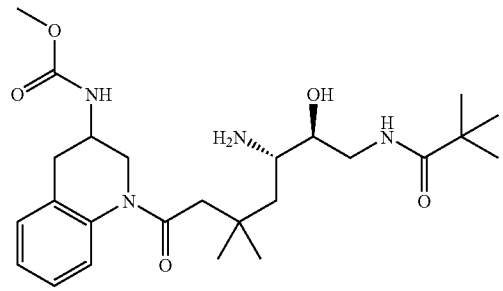

Analogously to Method A, 0.033 g of {1-[5(S)-tert-butoxycarbonylamino-7-(2,2-dimethyl-propionylamino)-6(S)-hydroxy-3,3-dimethyl-heptanoyl]-1,2,3,4-tetrahydro-quinolin-3(R,S)-yl}-carbamic acid methyl ester are used to prepare the title compound which is obtained as a white solid. Rf=0.41 (200:40:1 dichloromethane-methanol-25% conc. ammonia); Rt=3.35 (gradient I).

The starting materials are prepared as follows:

a) {1-[5(S)-tert-butoxycarbonylamino-7-(2,2-dimethyl-propionylamino)-6(S)-hydroxy-3,3-dimethyl-heptanoyl]-1,2,3,4-tetrahydro-quinolin-3(R,S)-yl}-carbamic acid methyl ester To a solution of 0.030 g of [1-(7-amino-5(S)-tert-butoxycarbonylamino-6(S)-hydroxy-3,3-dimethyl-heptanoyl)-1,2, 3,4-tetrahydro-quinolin-3(R,S)-yl]-carbamic acid methyl ester in 0.6 ml of ethyl acetate at room temperature under argon is added 0.6 ml of saturated aqueous sodium carbonate solution. The mixture is stirred for 15 minutes at room temperature and and 0.011 ml of pivaloyl chloride are added. The mixture is stirred at room temperature for 1.5 hours. The layers are separated and the aqueous layer is extracted with ethyl acetate (2×). The combined organic layers are dried over sodium sulphate, filtered and concentrated. The title compound is obtained as a beige oil from the residue by means of flash chromatography (SiO2 60 F). Rt=4.46 (gradient I).

b) [1-(7-amino-5(S)-tert-butoxycarbonylamino-6(S)-hydroxy-3,3-dimethyl-heptanoyl)-1,2,3,4-tetrahydro-quinolin-3(R,S)-yl]-carbamic acid methyl ester A mixture of 0.37 g of [1-(7-azido-5(S)-tert-butoxycarbonylamino-6(S)-hydroxy-3,3-dimethyl-heptanoyl)-1,2,3,4-tetrahydro-quinolin-3(R,S)-yl]-carbamic acid methyl ester and 75 mg of 10% Pd/C in 15 ml of methanol is hydrogenated at room temperature for 2 hours. The solid is removed by filtration over Hyflo® and the solution is concentrated. The title compound is obtained as a yellow oil from the residue by means of flash chromatography (SiO2 60 F). Rf=0.12 (200: 40:1 dichloromethane-methanol-25% conc. ammonia); Rt=3.43 (gradient I).

c) [1-(7-Azido-5(S)-tert-butoxycarbonylamino-6(S)-hydroxy-3,3-dimethyl-heptanoyl)-1,2,3,4-tetrahydro-quinolin-3(R,S)-yl]-carbamic acid methyl ester To a solution of 0.50 g of [1-(5(S)-tert-butoxycarbonylamino-3,3-dimethyl-5-(R)-oxiranyl-pentanoyl)-1,2,3,4-tetrahydro-quinolin-3(R,S)-yl]-carbamic acid methyl ester (Example 1b) in 10 ml of methanol at room temperature is added 0.17 g of sodium azide and 0.10 g of ammonium chloride. The mixture is stirred at reflux for 9 hours. The mixture is poured into ice and water and extracted with tert-butyl methyl ether (2×). The combined organic layers are washed with water and brine, dried over sodium sulphate, filtered and concentrated. The title compound is obtained as a yellow oil from the residue by means of flash chromatography (SiO2 60 F). Rf=0.3 (2:1 EtOAc-heptane); Rt=4.41 (gradient I).

EXAMPLE 19

(1-{5(S)-Amino-6(S)-hydroxy-3,3-dimethyl-7-[2-methyl-2-tetrahydro-pyran-4-yl)-propionylamino]-heptanoyl}-1,2,3,4-tetrahydro-quinolin-3(R,S)-yl)-carbamic acid methyl ester hydrochloride

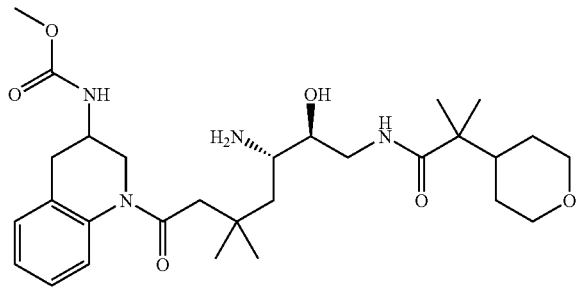

Analogously to Method A, 0.044 g of (1-{5(S)-tert-butoxycarbonylamino-6-(hydroxy-3,3-dimethyl-7-[2-methyl-2-(tetrahydro-pyran-4-yl)-propionylamino]-heptanoyl}-1,2,3,4-tetrahydro-quinolin-3(R,S)-yl)-carbamic acid methyl ester are used to prepare the title compound which is obtained as a white solid. Rf=0.43 (200:40:1 dichloromethane-methanol-25% conc. ammonia); Rt=3.28 (gradient I).

The starting material is prepared as follows:

a) (1-{5(S)-tert-butoxycarbonylamino-6(S)-hydroxy-3,3-dimethyl-7-[2-methyl-2-(tetrahydro-pyran-4-yl)-propionylamino]-heptanoyl}-1,2,3,4-tetrahydro-quinolin-3(R,S)-yl)-carbamic acid methyl ester To a solution of 0.017 g of 2-methyl-2-(tetrahydro-pyran-4-yl)-propionic acid in 1 ml of methylene chloride under argon at 0° C. is added 0.021 ml of 1-chloro-N,N-2-trimethylpropenylamine. The mixture is stirred for 1 hour, concentrated, and the residue dissolved in 0.6 ml ethyl acetate. This solution is added to a mixture of 0.030 g of [1-(7-amino-5(S)-tert-butoxycarbonylamino-6(S)-hydroxy-3,3-dimethyl-heptanoyl-1,2,3,4-tetrahydro-quinolin-3(R,S)-yl]-carbamic acid methyl ester (Example 18b) in 0.6 ml of ethyl acetate and 0.6 ml of saturated aqueous sodium carbonate. After stirring at room temperature for 1.5 hours, the layers are separated and the aqueous layer is extracted with ethyl acetate (2×). The combined organic layers are dried over sodium sulphate, filtered and concentrated. The title compound is obtained as a beige oil from the residue by means of flash chromatography (SiO2 60 F). Rt=4.32 (gradient I).

According to the processes described in Examples 18 and 19, the following compounds are prepared in an analogous manner:

| Examples: | |
|---|---|
| 20 | {1-[5(S)-Amino-7-(2-cyclohexyl-2-methyl-propionylamino)-6(S)-hydroxy-3,3-dimethyl-heotanoyl]-1,2,3,4-tetrahydro-quinolin-3(R,S)-yl}-carbamic acid methyl ester hydrochloride |
| 21 | (1-{5(S)-Amino-6(S)-hydroxv-3,3-dimethyl-7-[(1-phenyl-cyclobutanecarbonyl)-amino]-heptanoyl}-1,2,3,4-tetrahydro-quinolin-3(R,S)-yl)-carbamic acid methyl ester hydrochloride |
| 22 | {1-[5(S)-Amino-7-(2,2-dimethy-hexanoylamino)-6(S)-hydroxy-3,3-dimethyl-heptanoyl]-1,2,3,4-tetrahydro-quinolin-3(R,S)-yl}-carbamic acid methyl ester hydrochloride |
| 23 | [1-(5(S)-Amino-7-{[1-(4-chloro-pheny)-cyclobutanecarbonyl]-amino}-6(S)-hydroxy-3,3-dimethyl-heptanoyl}-1,2,3,4-tetrahydro-quinolin-3(R,S)-yl]-carbamic acid methyl ester hydrochloride |
| 24 | {1-[5(S)-Amino-6(S)-hydroxy-3,3-dimethyl-7-(2-methyl-2-morpholin-4-yl-propionylamino)-heptanoyl]-1,2,3,4-tetrahydro-quinolin-3(R,S)-yl}-carbamic acid methyl ester dihydrochloride |
| 25 | (1-{5(S)-Amino-7-[2-(3-fluoro-phenyl)-2-methyl-propionylamino]-6(S)-hydroxy-3,3-dimethyl-heptanoyl}-1,2,3,4-tetrahydro-quinolin-3(R,S)-yl)-carbamic acid methyl ester hydrochloride |
| 26 | (1-{5(S)-Amino-7-[(1-cyclohexyl-cyclobutanecarbonyl)-amino]-6(S)-hydroxy-3,3-dimethyl-heptanol}-1,2,3,4-tetrahydro-quinolin-3(R,S)-yl)-carbamic acid methyl ester hydrochloride |
| 27 | {1-[5(S)-Amino-6(S)-hydroxy-3,3-dimethyl-7-(2-methyl-2-pyridin-3-yl-propionylamino)-heptanoyl]-1,2,3,4-tetrahydro-quinolin-3(R,S)-yl}-carbamic acid methyl ester dihydrochloride |
| 28 | {1-[5(S)-Amino-4-(3-chloro-2,2-dimethyl-propionylamino)-6(S)-hydroxy-3,3-dimethyl heptanoyl]-1,2,3,4-tetrahydro-quinolin-3(R,S)-yl}-carbamic acid methyl ester hydrochloride |
| 29 | {1-[7-(2-Acetylamino-2-methyl-propuinylamino)-5(S)-Amino-6(S)-hydroxy-3,3-dimethyl-heptanoyl]-1,2,3,4-tetrahydro-quinolin-3(R,S)-yl}-carbamic acid methyl ester hydrochloride |

-continued

Examples:

| | |
|---|---|
| 30 | (1-{5(S)-Amino-6(S)-hydrozy-3,3-dimethyl-7-[(1-trifluoromethyl-cyclobutanecarbonyl)-amino]-heptanoyl}-1,2,3,4-tetrahydro-quinolin-3(R,S)-yl)-carbamic acid methyl ester hydrochloride |
| 31 | {1-[5(S)-Amino-7-(2-cyclohexyloxy-2-methyl-propionylamino)-6(S)-hydrozy-3,3-dimethyl-heptanoyl]-1,2,3,4-tetrahydro-quinolin-3(R,S)-yl}-carbamic acid methyl ester hydrochloride |
| 32 | {1-[5(S)-Amino-6(S)-hydroxy-7-(2-methoxy-2-methyl-propionylamino)-3,3-dimethyl-heptanoyl]-1,2,3,4-tetrahydro-quinolin-3(R,S)-yl}-carbamic acid methyl ester hydrochloride |
| 33 | {1-]5(S)-Amino-6(S)-hydroxy-3,3-dimethyl-7-(2-methyl-2-piperidin-1-yl-propionylamino)-heptanoyl]-1,2,3,4-tetrahydro-quinolin-3(R,S)-yl}-carbamic acid methyl ester dihydrochloride |
| 34 | (1-[5(S)-Amino-6(S)-hydrozy-3,3-dimethyl-7-[(1-methyl-cyclohexanecarbonyl)-amino]-heptanoyl}-1,2,3,4-tetrahydro-quinolin-3(R,S)-yl)-carbamic acid methyl ester hydrochloride |
| 35 | (1-{5(S)-Amino-6(S)-hydroxy-7-[2-(1H-indol-3-yl)-2-methyl-propionylamino]-3,3-dimethyl-heptanoyl}-1,2,3,4-tetrahydro-quinolin-3(R,S)-yl)-carbamic acid methyl ester hydrochloride |
| 36 | {1-[5(S)-Amino-6(S)-hydroxy-7-(2(R)-methoxy-propionylamino)-3,3-dimethyl-heptanoyl]-1,2,3,4-tetrahydro-quinolin-3(R,S)-yl}-carbamic acid methyl ester hydrochloride |
| 37 | (1-{7-[(Adamantane-1-carbonyl)-amino]-5(S)-Amino-6(S)-hydroxy-3,3-dimethyl-heptanoyl}-1,2,3,4-tetrahydro-quinolin-3(R,S)-yl)-carbamic acid methyl ester hydrochloride |
| 38 | (1-{5(S)-Amino-7-[(2,2-dimethyl-propionyl)-hydroxy-amino]-6(S)-hydroxy-3,3-dimethyl-heptanoyl}-1,2,3,4-tetrahydro-quinolin-3(R,S)-yl)-carbamic acid methyl ester hydrochloride |
| 39 | {1-[5(S)-Amino-7-(3,3-dimethyl-ureido)-6(S)-hydroxy-3,3-dimethyl-heptanoyl]-1,2,3,4-tetrahydro-quinolin-3(R,S)-yl}-carbamic acid methyl ester hydrochloride |
| 40 | [1-(5(S)-Amino-7-benzoylamino-6(S)-hydroxy-3,3-dimethyl-heptanoyl)-1,2,3,4-tetrahydro-quinolin-3(R,S)-yl]-carbamic acid methyl ester hydrochloride |
| 41 | {1-[7-(Acetyl-methyl-amino)-5(S)-Amino-6(S)-hydroxy-3,3-dimethyl-heptanoyl]-1,2,3,4-tetrahydro-quinolin-3(R,S)-yl}-carbamic acid methyl ester hydrochloride |
| 42 | {1-[5(S)-Amino-6(S)-hydroxy-3,3-dimethyl-7-(3,3,3-trifluoro-2(R)-methoxy-2-phenyl-propionylamino)-heptanoyl]-1,2,3,4-tetrahydro-quinolin-3(R,S)-yl}-carbamic acid methyl ester hydrochloride |
| 43 | {1-[7-(N-Acetyl-hydrazino)-5(S)-Amino-6(S)-hydrozy-3,3-dimethyl-heptanoyl]-1,2,3,4-tetrahydro-quinolin-3(R,S)-yl}-carbamic acid methyl ester dihydrochloride |
| 44 | {1-[5(S)-Amino-6(S)-hydroxy-7-(2-methoxy-3-phenyl-propionylamino)-3,3-dimethyl-heptanoyl]-1,2,3,4-tetrahydro-quinolin-3(R,S)-yl}-carbamic acid methyl ester hydrochloride |
| 45 | {1-[5(S)-Amino-7-(3-cyclohexyl-2-methoxy-propionylamino)-6(S)-hydroxy-3,3-dimethyl-heptanoyl]-1,2,3,4-tetrahydro-quinolin-3(R,S)-yl}-carbamic acid methyl ester hydrochloride |
| 46 | (1-{5(S)-Amino-6(S)-hydroxy-7-[2-(1H-imidazol-4-yl)-2-methyl-propionylamino]-3,3-dimethyl-heptanoyl}-1,2,3,4-tetrahydro-quinolin-3(R,S)-yl)-carbamic acid methyl ester hydrochloride |
| 47 | {1-[5(S)-Amino-7-(2,2-dimethyl-4-methylamino-butyrylamino)-6(S)-hydroxy-3,3-dimethyl-heptanoyl]-1,2,3,4-tetrahydro-quinolin-3(R,S)-yl}-carbamic acid methyl ester dihydrochloride |
| 48 | (1-{5(S)-Amino-6(S)-hydroxy-7-[(2(S)-hydroxy-(S)-cyclopentanecarbonyl)-amino]-3,3-dimethyl-heptanoyl}-1,2,3,4-tetrahydro-quinolin-3(R,S)-yl)-carbamic acid methyl ester hydrochloride |
| 49 | (1-{5(S)-Amino-6(S)-hydroxy-7-[2-(1,2-dihydro-spiro[3H-indole-3,4'-piperidin]-1'-yl)-2-methyl-propionylamino]-3,3-dimethyl-heptanoyl}-1,2,3,4-tetrahydro-quinolin-3(R,S)-yl)-carbamic acid methyl ester dihydrochloride |
| | 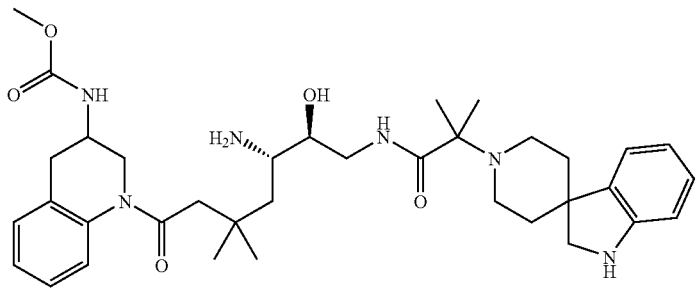 |
| 50 | (1-{5(S)-Amino-6(S)-hydroxy-7-[2-(cis-4-hydroxy-cyclohex-1-yl)-2-methyl-propionylamino]-3,3-dimethyl-heptanoyl]-1,2,3,4-tetrahydro-quinolin-3(R,S)-yl)-carbamic acid methyl ester hydrochloride |

The starting materials are prepared as follows:

a) 2-(cis-4-Hydroxy-cyclohexyl)-2-methyl-propionic acid 0.200 g of 2-(cis-4-hydroxy-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is then neutralised with 1M HCl and concentrated by evaporation. The title compound is identified from the residue by means of flash chromatography (SiO2 60 F) based on its Rf value.

b) 2-(cis-4-Hydroxy-cyclohexyl)-2-methyl-propionic acid methyl ester and 2-(trans-4-Hydroxy-cyclohexyl)-2-methyl-propionic acid methyl ester A solution of 2.0 g of 2-(cis/trans-4-hydroxy-cyclohexyl)-2-methyl-propionic acid in 40 ml of methanol is cooled to 0° C. 20 ml of a 2M trimethysilyidiazomethane solution in hexanes are added dropwise and the reaction solution is left to stand at room temperature for 1 hour. The solution is concentrated under reduced pressure and the residue taken up in ethyl acetate. The solution is washed with saturated aqueous sodium carbonate solution and brine, dried over sodium sulphate and concentrated by evaporation. The residue is purified by flash chromatography (SiO2 60 F) to provide the title compounds as colourless oils, the cis isomer eluting first. Rf (cis)=0.11 (1:3 EtOAc-heptane); Rf (trans)=0.09 (1:3 EtOAc-heptane).

c) 2-(cis/trans-4-Hydroxy-cyclohexyl)-2-methyl-propionic acid 2.690 g of 2-(4-hydroxy-phenyl)-2-methyl-propionic acid (29913-51-7) are dissolved in 20 ml of water and 30 ml of 1M NaOH solution. 0.200 g of Raney-Nickel are added and the reaction mixture is hydrogenated at 50 bar and 150° C. for 24 hours. The catalyst is removed by filtration over Hyflo and the filtrate is concentrated by evaporation. The residue is taken up in 200 ml of water and the solution neutralized with 1M HCl to pH 6. The reaction mixture is then extracted with dichloromethane (2×200 ml) and ethyl acetate (2×20 ml) and the combined organic phases are dried over sodium sulphate and concentrated by evaporation to provide the title compounds as a ca. 1:4 mixture of cis/trans-isomers. The white solid is used for the next step without further purification.

51 (1-{5(S)-Amino-6(S)-hydroxy-7-[2-(trans-4-hydroxy-cyclohex-1-yl)-2-methyl-propionylamino]-3,3-dimethyl-heptanoyl}-1,2,3,4-tetrahydro-quinolin-3(R,S)-yl)-carbamic acid methyl ester hydrochloride
52 (1-{5(S)-Amino-6(S)-hydroxy-7-[2-(cis-4-methoxy-cyclohex-1-yl)-2-methyl-propionylamino]3,3-dimethyl-heptanoyl}-1,2,3,4-tetrahydro-quinolin-3(R,S)-yl)-carbamic acid methyl ester hydrochloride The starting materials are prepared as follows:

a) 2-cis-4-Methoxy-cyclohexyl)-2-methyl-propionic acid 0.200 g of 2-(cis-4-methoxy-cyclohexyl)-2-methyl-propionic acid methyl ester are dissolved in 4 ml of methanol. 4 ml of a 1M aqueous lithium hydroxide solution is added and the mixture is stirred for 16 hours at room temperature. The reaction mixture is then neutralised with 1M HCl and concentrated under reduced pressure. The title compound is identified from the residue by means of flash chromatography (SiO2 60 F) based on its Rf value.

b) 2-(cis-4-Methoxy-cyclohexyl)-2-methyl-propionic acid methyl ester 0.500 g of 2-(cis-4-hydroxy-cyclohexyl)-2-methyl-propionic acid methyl ester (Example 50b) are dissolved in 5 ml of dry tetrahydrofuran. 0.120 g of sodium hydride (60% dispersion) is added in portions and the mixture stirred at 40° C. for 1 hour. Methyl iodide (0.233 ml) is added and the mixture heated to 40° C. for 5 hours. The reaction mixture is then cooled to room temperature, quenched with 5 ml of water and extracted with tert-butyl methyl ether (2×50 ml). The combined organic phases are dried over sodium sulphate and concentrated by evaporation. The title compound is identified from the residue by means of flash chromatography (SiO2 60 F) based on its Rf value.

53 (1-{5(S)-Amino-6(S)-hydroxy-7-[2-(trans-4-methoxy-cyclohex-1-yl-2-methyl-propionylamino]-3,3-dimethyl-heptanoyl}-1,2,3,4-tetrahydro-quinolin-3(R,S)-yl)-carbamic acid methyl ester hydrochloride
54 {-[5(S)-Amino-7-(2-cyclohexyl-2(R)-methoxy-acetylamino)-6(S)-hydroxy-3,3-dimethyl-heptanoyl]-1,2,3,4-tetrahydro-quinolin-3(R,S)-yl}-carbamic acid methyl ester hydrochloride The starting material is prepared as follows:

a) (R)-Cyclohexyl-methoxy-acetic acid

An autoclave is charged with a solution of 1.00 g of (R)-α-methoxy-phenyl acetic acid in 20 ml methanol. 0.100 g of Nishimura catalyst are added and the mixture is hydrogenated at 4 bar and 20° C. for 1 hour. The mixture is filtered over Hyflo and the filtrate concentrated by evaporation to provide the title compound as a colourless oil. The crude material is used without further purification. Rf=0.84 (150:54:10:1 dichloromethane-methanol-water-acetic acid)

55 {1-[5(S)-Amino-6(S)hydroxy-7-(2(R)-methoxy-2-phenyl-acetylamino)-3,3-dimethyl-heptanoyl]-1,2,3,4-tetrahydro-quinolin-3(R,S)-yl}-carbamic acid methyl ester hydrochloride
56 {1-[5(S)-Amino 6(S)-hydroxy-7-(2(R)-methoxy-3,3-dimethyl-butyrylamino)-3,3-dimethyl-heptanoyl]-1,2,3,4-tetrahydro-quinolin-3(R,S)-yl}-carbamic acid methyl ester hydrochloride
57 {1-[5(S)-Amino-6(S)-hydroxy-3,3-dimethyl-7-(3,3,3-trifluoro-2-methoxy-2-trifluoromethyl-propionylamino)-heptanoyl]-1,2,3,4-tetrahydro-quinolin-3(R,S)-yl}-carbamic acid methyl ester hydrochloride
58 {1-[5(S)-Amino-6(S)-hydroxy-3,3-dimethyl-7-(3,3,3-trifluoro-2(R)-methoxy-2-methyl-propionylamino)-heptanoyl]-1,2,3,4-tetrahydro-quinolin-3(R,S)-yl}-carbamic acid methyl ester hydrochloride
59 {1-[5(S)-Amino-6(S)-hydroxy-3,3-dimethyl-7-(3,3,3-trifluoro-2(S)-methoxy-2-methyl-propionylamino)-heptanoyl]-1,2,3,4-tetrahydro-quinolin-3(R,S)-yl}-carbamic acid methyl ester hydrochloride
60 {1-[5(S)-Amino-7-(2-cyclohexyl-3,3,3-trifluoro-2(R)-methoxy-propionylamino)-6(S)-hydroxy-3,3-dimethyl-heptanoyl]-1,2,3,4-tetrahydro-quinolin-3(R,S)-yl}-carbamic acid methyl ester hydrochloride
61 {1-[5(S)-Amino-7-(2-phenyl-2(R)-methoxy-propionylamino)-6(S)-hydroxy-3,3,-dimethyl-heptanoyl]-1,2,3,4-tetrahydro-quinolin-3(R,S)-yl}-carbamic acid methyl ester hydrochloride
62 {1-[5(S)-Amino-7-(2-cyclohexyl-2(R)-methoxy-propionylamino)-6(S)-hydroxy-3,3-dimethyl-heptanoyl]-1,2,3,4-tetrahydro-quinolin-3(R,S)-yl}-carbamic acid methyl ester hydrochloride -continued 63 (1-{5(S)-Amino-6(S)-hydroxy-7-[(1-methoxy-cyclopentanecarbonyl)-amino]-3,3-dimethyl-heptanoyl}-1,2,3,4-tetrahydro-quinolin-3(R,S)-yl)-carbamic acid methyl ester hydrochloride
64 (1-{5(S)-Amino-6(S)-hydroxy-7-[(1-methoxy-cyclohexanecarbonyl)-amino]-3,3-dimethyl-heptanoyl}-1,2,3,4-tetrahydro-quinolin-3(R,S)-yl)-carbamic acid methyl ester hydrochloride
74 {1[5(S)-Amino-6(S)-hydroxy-3,3-dimetyl-7-(2-methyl-2-piperidin-3(R,S)-yl-propionylamino)-heptanoyl]-1,2,3,4-tetrahydro-quinolin-3(R,S)-yl]-carbamic acid methyl ester dihydrochloride
75 (1-{5(S)Amino-6(S)-hydroxy-3,3-dimethyl-7-[2-methyl-2-(1-methyl-piperidin-3(R,S)-yl)-propionylamino]-heptanoyl}-1,2,3,4-tetrahydro-quinolin-3(R,S)-yl)-carbamic acid methyl ester dihydrochloride The starting materials are prepared as follows:

a) 2-Methyl-2-(1-methyl-piperidin-3(R,S)-yl)-propionic acid 0.200 g of 2-methyl-2-(1-methyl-piperidin-3(R,S)-yl)-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml). The organic phases are combined and concentrated by evaporation. The residue is purified by means of flash chromatography (SiO2 60 F) to provide the title compound as a colourless oil. Rf 0.15 (150:54:10:1 dichloromethane-methanol-acetic acid-water).

b) 2-Methyl-2-(1-methyl-piperidin-3(R,S)-yl)-propionic acid methyl ester 0.370 g of 2-methyl-2-piperidin-3(R,S)-yl-propionic acid methyl ester hydrochloride are dissolved in 0.5 ml of 3M NaOH. 2 ml of formic acid and 0.19 ml of formaldehyde (35% aqueous solution) are added and the reaction solution is warmed to 60° C. for 20 hours. The solution is cooled to room temperature, neutralised with 3M NaOH to pH 8-9 and extracted with dichloromethane (3×10 ml). The combined organic phases are washed with water (10 ml), dried over sodium sulphate and concentrated by evaporation. The residue is purified by means of flash chromatography (SiO2 60 F) to provide the title compound as a colourless oil. Rf 0.19 (200:20:1 dichlormethane-methanol-25% conc. ammonia).

c) Methyl 2-methyl-2-piperidin-3(R,S)-ylpropionate hydrochloride 0.115 g of methyl 2-methyl-2-pyridin-3-ylpropionate (CAS 476429-23-9) is dissolved in an autoclave in 5 ml of methanol. The solution is admixed with 0.35 ml of 1.2M HCl in methanol and 0.012 g of platinum(IV) oxide, and the reaction mixture is hydrogenated at 4 bar and 23° over 46 hours. The catalyst is filtered off through Hyflo and the filtrate is concentrated by evaporation to give the crude title compound which is used directly in the next step.

76 {1-[5(S)-Amino-6(S)-hydroxy-3,3-dimethyl-7-(2-methyl-2-piperidin-2(R,S)-yl-propionylamino)-heptanoyl]-1,2,3,4-tetrahydro-quinolin-3(R,S)-yl}-carbamic acid methyl ester dihydrochloride
77 (1-{5(S)-Amino-6(S)-hydroxy-3,3-dimethyl-7-[2-methyl-2-(1-methyl-piperidin-2(R,S)-yl)-propionylamino]-heptanoyl}-1,2,3,4-tetrahydro-quinolin-3(R,S)-yl)-carbamic acid methyl ester dihydrochloride -continued 78 (1-{5(S)-Amino-6(S)-hydroxy-7-[2(R,S)-(trans-2-hydroxy-cyclohexyl)-2-methyl-propionylamino]-3,3-dimethyl-heptanoyl}-1,2,3,4-tetrahydro-quinolin-3(R,S)-yl)-carbamic acid methyl ester hydrochloride The starting material is prepared as follows:

a) trans-2-[2-tert-Butyl-dimethyl-silanyloxy)-cyclohexyl]-2-methyl-propionic acid Imidazole (0.310 g) is added to a solution of 0.337 g trans-(2-2-hydroxy-cyclohexyl)-2-methyl propionic acid (34440-72-7) and 0.682 g tert-butyl-dimethyl-chlorosilane in 7 ml of dry N,N-dimethylformamide. The mixture is left to stand at room temperature for 2 hours and is then warmed to 50° for 12 hours. The reaction mixture is poured onto water (30 ml) and the mixture is extracted with tert-butyl methyl ether (2×50 ml). The combined organic phases are washed with saturated aqueous sodium bicarbonate solution (30 ml) and brine (30 ml), dried over sodium sulphate and concentrated under reduced pressure. The residue is taken up in 9 ml of methanol and 3 ml of tetrahydrofuran and the resulting mixture is treated for 1 hour at room temperature with a 10% aqueous potassium carbonate solution (3 ml). The reaction solution is concentrated under reduced pressure to half of the initial volume and the pH is adjusted to 6 with 1M HCl. The mixture is extracted with tert-butyl methyl ether (2×60 ml) and the combined organic phases are washed with brine, dried over sodium sulphate and concentrated under reduced pressure. The residue is purified by means of flash chromatography (SiO2 60 F) to provide the title compound as white solid. Rf 0.64 (1:2 EtOAc-heptane).

79 (1-{5(S)-Amino-6(S)-hydroxy-7-[2(R,S)-(3(S)-hydroxy-cyclohex-1(R)-yl)-2-methyl-propionylamino]-3,3-dimethyl-heptanoyl}-1,2,3,4-tetrahydro-quinolin-3(R,S)-yl)-carbamic acid methyl ester hydrochloride The starting materials are prepared as follows:

a) 2-(3(S)-Hydroxy-cyclohex-1(R)-yl)-2-methyl-propionic acid 1.00 g of 2-(cis-3-hydroxy-cyclohexyl)-2-methyl-propionic acid ethyl ester are dissolved in 30 ml of methanol. 30 ml of a 1M aqueous lithium hydroxide solution are added and the mixture is stirred for 16 hours at room temperature. The reaction mixture is neutralised with 1M HCl and concentrated by evaporation. The title compound is identified from the residue by means of flash chromatography (SiO2 60 F) based on its Rf value.

b) 2-(3(S)-Hydroxy-cyclohex-1(R)-yl)-2-methyl-propionic acid ethyl ester 3 ml of 1M tetrabutylammonium fluoride solution in tetrahydrofuran are added to a solution of 1.00 g of 2-[3(S)-(tert-butyl-dimethylsilanyloxy)-cyclohex-(1R)-yl]-2-methyl-propionic acid ethyl ester in 3 ml of tetrahydrofuran at 0° C. The reaction is left to stand at room temperature for 1 hour and is then diluted with tert-butyl methyl ether (20 ml) and washed with water (20 ml) and brine (20 ml). The organic layer is dried over sodium sulphate and concentrated by evaporation.

The title compound is identified from the residue by means of flash chromatography (SiO2 60 F) based on its Rf value.

c) 2-[3(S)-(tert-Butyl-dlimethylsilanyloxy)-cyclo-hex-1(R)-yl]-2-methyl-propionic acid ethyl ester A solution of 21 ml lithium diisopropylamide (ca. 1M in tetrahydrofuran/hexanes) is cooled to −78° b. A solution of 3.72 g [3(S)-(tert-butyl-dimethyl-silanyl-oxy)-cyclohex-1(R)-yl]-acetic acid ethyl ester (197091-18-2) in 20 ml of tetrahydrofuran is added dropwise over a period of 15 minutes while maintaining the temperature at −78° C. The reaction solution is stirred for 30 minutes at −78° C. and methyl iodide (1.31 ml) is added in one portion. The reaction mixture is warmed to 0° C. over a period of 30 minutes and is then cooled again to −78° C. Lithium diisopropylamide-solution (21 ml) is added dropwise over a period of 15 minutes and the reaction mixture is stirred for 30 minutes at −78° C. 1.31 ml Methyl iodide are added in one portion and the reaction mixture is warmed to room temperature over a period of 16 hours. The reaction mixture is quenched with 0.1M HCl (50 ml) and is then extracted with tert-butyl methyl ether (3×50 ml). The combined organic phases are washed with brine (50 ml), dried over sodium sulphate and concentrated by evaporation. The title compound is identified from the residue by means of flash chromatography (SiO2 60 F) based on its Rf value.

---

80 {1-[5(S)-Amino-6(S)-hydroxy-7-(2-imidazol-1-yl-2-methyl-propionylamino)-3,3-dimethyl-heptanoyl]-1,2,3,4-tetrahydro-quinolin-3(R,S)-yl}-carbamic acid methyl ester dihydrochloride

---

The starting material is prepared as follows:

a) 2-Imidazol-1-yl-2-methyl-propionic acid 1.54 g of 2-imidazol-1-yl-2-methyl-propionic acid ethyl ester (73828-88-3) are dissolved in 20 ml of methanol. 20 ml of a 3M NaOH are added and the mixture is stirred for 16 hours at 60° C. The reaction mixture is then neutralised with 1M HCl and concentrated by evaporation. The title compound is identified from the residue by means of flash chromatography (SiO2 60 F) based on its Rf value.

---

81 {1-[5(S)-Amino-7-(2-cyano-2,2-dimethyl-acetylamino)-6(S)-hydroxy-3,3-dimethyl-heptanoyl]-1,2,3,4-tetrahydro-quinolin-3(R,S)-yl}-carbamic acid methyl ester hydrochloride
82 (1-{7-[2-(trans-4-Acetylamino-cyclohexyl)-2-methyl-propionylamino]-5(S)-amino-6(S)-hydroxy-3,3-dimethyl-heptanoyl}-1,2,3,4-tetrahydro-quinolin-3(R,S)-yl)-carbamic acid methyl ester hydrochloride

---

The starting materials are prepared as follows:

a) trans-2-(4-Acetylamino-cyclohexyl)-2-methyl-propionic acid 0.200 g of trans-2-(4-acetylamino-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml)—the combined organic phases are concentrated by evaporation. The title compound is identified from the residue by means of flash chromatography (SiO2 60 F) based on its Rf value.

b) trans-2-(4-Acetylamino-cyclohexyl)-2-methyl-propionic acid methyl ester

A round bottom flask is charged with 0.422 g of trans-2-(4-azido-cyclohexyl)-2-methyl-propionic acid methyl ester. 0.71 ml of thiocetic acid are added and the solution is stirred for 1 hour at room temperature. After completion of the reaction, the reaction mixture is concentrated by evaporation. The title compound is identified from the residue by means of flash chromatography (SiO2 60 F) based on its Rf value.

c) trans-2-(4-Azido-cyclohexyl)-2-methyl-propionic acid methyl ester

Sodium azide (0.761 g) is added to a solution of 0.898 g of cis-2-(4-methanesulfonyloxy-cyclohexyl)-2-methyl-propionic acid methyl ester in 7 ml of N,N-dimethylformamide. The reaction mixture is warmed to 100° C. for 16 hours. The mixture is cooled to room temperature, diluted with 20 ml of water and extracted with tert-butyl methyl ether (3×30 ml). The combined organic phases are washed with brine (20 ml), dried over sodium sulphate and concentrated by evaporation. The title compound is identified from the residue by means of flash chromatography (SiO2 60 F) based on its Rf value.

d) cis-2-(4-Methanesulfonyloxy-cyclohexl)-2-methyl-propionic acid methyl ester

A solution of 1.00 g of 2-(cis-4-hydroxy-cyclohexyl)-2-methyl-propionic acid methyl ester (Example 50b), 1.38 ml triethylamine and 0.061 g of 4-dimethylaminopyridine in 20 ml of dichloromethane is cooled to 0° C. Methanesulfonychloride (0.50 ml) is added and the solution is left to stand at room temperature for 16 hours. The solution is poured onto saturated aqueous sodium hydrogen carbonate solution and the phases are separated. The aqueous phase is extracted with dichloromethane (2×50 ml)—the combined organic phases are washed with brine (50 ml), dried over sodium sulphate and concentrated by evaporation.

The title compound is identified from the residue by means of flash chromatography (SiO2 60 F) based on its Rf value.

---

83 (1-{7-[2-(cis-3-Acetylamino-cyclohexyl)-2-methyl-propionylamino]-5(S)-amino-6(S)-hydroxy-3,3-dimethyl-heptanoyl}-1,2,3,4-tetrahydro-quinolin-3(R,S)-yl)-carbamic acid methyl ester hydrochloride

---

The starting materials are prepared according to the processes described in Example 152 starting from 2-(3(S)-hydroxy-cyclohex-1(R)-yl)-2-methyl-propionic acid ethyl ester (Example 79b).

---

84 {1-[5(S)-Amino-7-(2,2-difluoro-2-phenyl-acetylamino)-6(S)-hydroxy-3,3-dimethyl-heptanoyl]-1,2,3,4-tetrahydro-quinolin-3(R,S)-yl}-carbamic acid methyl ester hydrochloride
85 {1-[5(S)-Amino-7-(2-cyclohexyl-2,2-difluoro-acetylamino)-6(S)-hydroxy-3,3-dimethyl-heptanoyl]-1,2,3,4-tetrahydro-quinolin-3(R,S)-yl}-carbamic acid methyl ester hydrochloride
86 (1-{5(S)-Amino-7-[2,2-difluoro-2-(tetrahydro-pyran-4-yl)-acetyl-amino]-6(S)-hydroxy-3,3-dimethyl-heptanoyl}-1,2,3,4-tetrahydro-quinolin-3(R,S)-yl)-carbamic acid methyl ester hydrochloride

EXAMPLE 65

{1-[5(S)-Amino-6(S)-hydroxy-3,3-dimethyl-7-(2-oxo-piperidin-1-yl)-heptanoyl]-1,2,3,4-tetrahydro-quinolin-3(R,S)-yl}-carbamic acid methyl ester hydrochloride

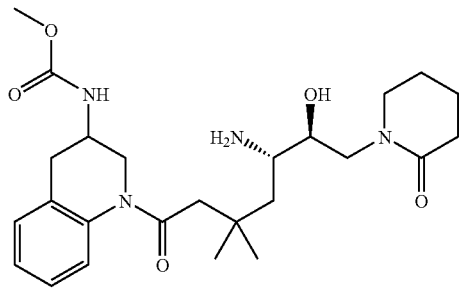

A solution of 0.051 g of (1-{3,3-dimethyl-4-[2-oxo-5(S)-(2-oxo-piperidin-1-ylmethyl)-oxazolidin-4(S)-yl]-butyryl}-1,2,3,4-tetrahydro-quinolin-(R,S)-yl)-carbamic acid methyl ester and 0.050 g lithium hydroxide hydrat in 1.5 ml ethanol und 1.5 ml wasser is stirred at 100° C. for 2 hours. The reaction mixture is cooled to room temperature, poured into ice and water and extracted with ethyl acetate (3×). The combined organic layers are dried over sodium sulphate, filtered and concentrated. The free base of the title compound is identified from the residue by means of flash chromatography (SiO2 60 F) based on its Rf value. This is dissolved in 1 ml dioxane, diluted with 0.040 ml 4N HCl (in dioxane), frozen in liquid nitrogen and lyophilized to give the title compound.

The starting material is prepared as follows:

a) (1-{3,3-dimethyl-4-[2-oxo-5(S)-(2-oxo-piperidin-1-ylmethyl)-oxazolidin-4(S)-yl]-butyryl}-1,2,3,4-tetrahydro-quinolin-3(R,S)-yl)-carbamic acid methyl ester A mixture of 0.115 g piperidin-2-one and 0.136 g potassium tert-butoxide in 3 ml dimethylsulfoxide is stirred at room temperature for 30 minutes, charged with 0.256 g [1-(5(S)-tert-butoxycarbonylamino-3,3-dimethyl-5-(R)-oxiranyl-pentanoyl)-1,2,3,4-tetrahydro-quinolin-3(R,S)-yl]-carbamic acid methyl ester (Example 1b), and then stirred overnight. The reaction mixture is poured into a mixture of ice and water and extracted with tert-butyl methyl ether (2×). The combined organic layers are washed with water and brine, dried over sodium sulphate, filtered and concentrated. The title compound is identified from the residue by means of flash chromatography (SiO2 60 F) based on its Rf value.

According to the process described in Example 65, the following compounds are prepared in an analogous manner.

| Examples: | |
|---|---|
| 66 | {1-[5(S)-Amino-7-(3,3-dimethyl-2-oxo-pyrrolidin-1-yl)-6(S)-hydroxy-3,3-dimethyl-heptanoyl]-1,2,3,4-tetrahydro-quinolin-3(R,S)-yl}-carbamic acid methyl ester hydrochloride |
| 67 | {1-[5(S)-Amino-6(S)-hydroxy-7-(4(R)-hydroxy-2-oxo-pyrrolidin-1-yl)-3,3-dimethyl-heptanoyl]-1,2,3,4-tetrahydro-quinolin-3(R,S)-yl}-carbamic acid methyl ester hydrochloride |
| 68 | {1-[5(S)-Amino-6(S)-hydroxy-3,3-dimethyl-7-(2-oxo-tetrahydro-pyrimidin-1-yl)-heptanoyl]-1,2,3,4-tetrahydro-quinolin-3(R,S)-yl}-carbamic acid methyl ester hydrochloride |

EXAMPLE 69

{1-[5(S)-Amino-6(S)-hydroxy-3,3-dimethyl-7-(propane-2-sulfonylamino)-heptanoyl]-1,2,3,4-tetrahydro-quinolin-3(R,S)-yl}carbamic acid methyl ester hydrochloride

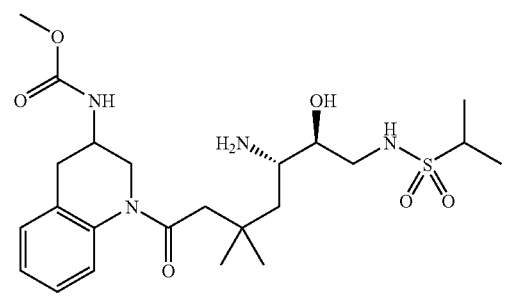

0.007 ml Propan-2-sulfonyl chlorid are added to a solution of 0.026 g [1-(7-amino-5(S)-tert-butoxycarbonylamino-6(S)-hydroxy-3,3-dimethyl-heptanoyl)-1,2,3,4-tetrahydro-quinolin-3(R,S)-yl]-carbamic acid methyl ester (Example 18b) and 0.007 ml triethylamine in 1 ml dichlormethane at 0° C. After 5 hours, the reaction mixture is concentrated. The intermediate N-Boc derivative is identified from the residue by means of flash chromatography (SiO2 60 F) based on its Rf value. This is dissolved in 0.82 ml 4N HCl (in dioxane), stirred for 4 hours and concentrated. The residue is dissolved in 0.5 ml tert-butanol, frozen in liquid nitrogen and lyophilized to give the title compound which is identified from the residue based on its Rf value.

According to the process described in Example 69, the following compounds are prepared in an analogous manner:

| Examples: | |
|---|---|
| 70 | [1-(5(S)-Amino-7-cyclopropanesulfonylamino-6(S)-hydroxy-3,3-dimethyl-heptanoyl)-1,2,3,4-tetrahydro-quinolin-3(R,S)-yl-carbamic acid methyl ester hydrochloride |
| 71 | [1-(5(S)-Amino-6(S)-hydroxy-3,3-dimethyl-7-phenylmethanesulfonylamino-heptanoyl)-1,2,3,4-tetrahydro-quinolin-3(R,S)-yl]-carbamic acid methyl ester hydrochloride |
| 72 | {1-[5(S)-Amino-6(S)-hydroxy-3,3-dimethyl-7-(thiophene-2-sulfonylamino)-heptanoy1]-1,2,3,4-tetrahydro-quinolin-3(R,S)-yl-carbamic acid methyl ester hydrochloride |
| 73 | [1-(5(S)-Amino-7-benzenesulfonylamino-6(S)-hydroxy-3,3-dimethyl-heptanoyl)-1,2,3,4-tetrahydro-quinolin-3(R,S)-yl]-carbamic acid methyl ester hydrochloride |
| 87 | {1-[5(S)-Amino-6(S)-hydroxy-3,3-dimethyl-7-(2-methyl-propane-2-sulfonylamino)-heptanoyl]-1,2,3,4-tetrahydro-quinolin-3(R,S)-yl}-carbamic acid methyl ester hydrochloride |
| 88 | {1-[5(S)-Amino-7-(2-cyclohexyl-propane-2-sulfonylamino-6(S)-hydroxy-3,3-dimethyl-heptanoyl]-1,2,3,4-tetrahydro-quinolin-3(R,S)-yl}-carbamic acid methyl ester hydrochloride |

The starting materials are prepared as follows:

a) 2-Cyclohexyl-propane-2-sulfonyl chloride 2 mmol of phosphoroxytrichloride are added to a solution of 1 mmol of 2-cyclohexyl-propane-2-sulfonic acid in acetonitrile and the reaction mixture is heated to reflux for 2 hours. The reaction mixture is cooled to room temperature, carefully quenched by the addition of water and extracted with tert-butyl methyl ether. The organic phase is dried over sodium sulphate and concentrated by evaporation. The crude title compound is used without further purification.

b) 2-Cyclohexyl-propane-2-sulfonic acid 10 ml of an aqueous hydrogen peroxide solution (30% wt) are added to a stirred solution of 1 mmol of 2-cyclohexyl-propane-2-thiol in acetic and the mixture is then heated at 60° C. overnight. The reaction mixture is cooled to room temperature and the solvent removed under reduced pressure. The crude title compound is used without further purification.

c) 2-Cyclohexyl-propane-2-thiol 1 mmol of thiourea is added to a stirred solution of 1 mmol of (1-bromo-1-methyl-ethyl)-cyclohexane [BRN 2424910] in methanol and the mixture is stirred for 12 hours at room temperature. The solvent is removed under reduced pressure and the residue is then suspended in 10 ml of 2N NaOH and heated at 60° C. for 3 hours. The reaction mixture is cooled to room temperature and extracted with tert-butyl methyl ether (3×). The combined organic phases are dried over sodium sulphate and concentrated by evaporation. The crude title compound is used without further purification.

The invention claimed is:
1. A compound of the formula

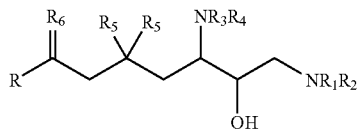

(I)

where
$R_1$ is a) hydrogen, amino or hydroxyl; or
is b) $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4, $C_1$-$C_8$-alkyl, halogen, cyano, oxide, oxo, trifluoromethyl, $C_1$-$C_8$-alkoxy, $C_1$-$C_8$-alkoxycarbonyl, aryl or heterocyclyl;
$R_2$ is a) $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_8$-cycloalkyl-$C_1$-$C_8$-alkanoyl, aryl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_{12}$-cycloalkyl, $C_3$-$C_8$-cycloalkoxy, amino, $C_1$-$C_6$-alkylamino, di-$C_1$-$C_6$-alkylamino, $C_1$-$C_6$-alkanoylamino, $C_1$-$C_6$-alkoxycarbonylamino, halogen, oxo, cyano, hydroxyl, oxide, trifluoromethyl, $C_1$-$C_8$-alkoxy, optionally N-mono- or N,N-di-$C_1$-$C_8$-alkylated carbamoyl-$C_0$-$C_8$-alkyl, optionally esterified carboxyl, $C_1$-$C_6$-alkylenedioxy, aryl or heterocyclyl; or
is b) together with $R_1$ and the nitrogen atom to which they are bonded a saturated or partly unsaturated 4-8-membered heterocyclic ring which may contain an additional nitrogen, oxygen or sulphur atom or a —SO— or —SO2- group, in which case the additional nitrogen atom may optionally be substituted by $C_1$-$C_8$-alkyl, $C_1$-$C_8$-alkanoyl, $C_1$-$C_8$-alkoxycarbonyl, aryl or heterocyclyl radicals, and this heterocyclic ring may be part of a bicyclic or tricyclic ring system having a total of up to 16 members and the second ring may also contain a nitrogen, oxygen or sulphur atom or a —SO— or —SO2- group, and the nitrogen atom in the second ring may optionally be substituted by $C_1$-$C_8$-alkyl, $C_1$-$C_8$-alkanoyl, $C_1$-$C_8$-alkoxycarbonyl, aryl or heterocyclyl radicals and all ring systems mentioned may be substituted by 1-4 $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_8$-cycloalkyl-$C_1$-$C_8$-alkanoyl, aryl-$C_1$-$C_8$-alkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, halogen, hydroxyl, oxide, oxo, trifluoromethyl, $C_1$-$C_8$-alkoxy, $C_1$-$C_8$-alkoxy-$C_1$-$C_8$-alkoxy, $C_1$-$C_8$-alkoxy-$C_1$-$C_8$-alkyl, $C_1$-$C_8$-alkoxycarbonylamino, $C_1$-$C_8$-alkanoylamino, $C_1$-$C_8$-alkyl-amino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy or heterocyclyloxy-$C_0$-$C_4$-alkyl-$C_1$-$C_8$-alkoxy;
$R_3$ is hydrogen, $C_1$-$C_8$-alkyl, $C_1$-$C_8$-alkoxycarbonyl or $C_1$-$C_8$-alkanoyl;
$R_4$ is hydrogen, $C_1$-$C_8$-alkyl, $C_1$-$C_8$-alkoxycarbonyl or $C_1$-$C_8$-alkanoyl;
$R_5$ are each independently hydrogen or $C_1$-$C_8$-alkyl or, together with the carbon atom to which they are bonded, are a $C_3$-$C_8$-cycloalkylidene radical;
$R_6$ is one oxygen atom or two hydrogen atoms;
R is optionally substituted heterocyclyl bonded via a ring nitrogen atom;
or salt or prodrug thereof, or where one or more atoms are replaced by their stable, non-radioactive isotopes.
2. A compound according to claim 1, where
$R_1$ a) is hydrogen; or
is b) $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4 $C_1$-$C_8$-alkyl, halogen, cyano, oxide, oxo, trifluoromethyl, $C_1$-$C_8$-alkoxy, $C_1$-$C_8$-alkoxycarbonyl, aryl or heterocyclyl;
$R_2$ is a) $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_8$-cycloalkyl-$C_1$-$C_8$-alkanoyl, aryl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, amino, $C_{1-6}$-alkylamino, di-$C_{1-6}$-alkylamino, $C_0$-$C_6$-alkylcarbonylamino, $C_1$-$C_6$-alkoxycarbonylamino, halogen, oxo, cyano, hydroxyl, oxide, trifluoromethyl, $C_1$-$C_8$-alkoxy, optionally N-mono- or N,N-di-$C_1$-$C_8$-alkylated carbamoyl-$C_0$-$C_8$-alkyl, optionally esterified carboxyl, $C_{1-6}$alkylenedioxy, aryl or heterocyclyl; or is b) together with $R_1$ and the nitrogen atom to which they are bonded, a saturated or partly unsaturated 4-8-membered heterocyclic ring which may contain an additional nitrogen, oxygen or sulphur atom or a —SO— or SO2-group, in which case the additional nitrogen atom may optionally be substituted by $C_1$-$C_8$-alkyl, $C_1$-$C_8$-alkanoyl, $C_1$-$C_8$-alkoxycarbonyl, aryl or heteroaryl radicals, and this heterocyclic ring may be part of a bicyclic or tricyclic ring system having a total of up to 16 members and the second ring may also contain a nitrogen, oxygen or sulphur atom or a —SO— or —SO2- group, and the nitrogen atom in the second ring may optionally be substituted by $C_1$-$C_8$-alkyl, $C_1$-$C_8$-alkanoyl, $C_1$-$C_8$-alkoxycarbonyl, aryl or heterocyclyl radicals, and all ring systems mentioned may be substituted by 1-4 $C_1$-$C_8$-alkyl, halogen, hydroxyl, cyano, oxide, oxo, trifluoromethyl, $C_1$-$C_8$-alkoxy, $C_1$-$C_8$-alkoxy-$C_1$-$C_8$-alkoxy, $C_1$-$C_8$-alkoxycarbonylamino, $C_0$-$C_8$-alkylcarbonylamino, $C_1$-$C_8$-alkylamino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy or heterocyclyloxy-$C_0$-$C_4$-alkyl-$C_1$-$C_8$-alkoxy;

$R_3$ is hydrogen, $C_1$-$C_8$-alkyl, $C_1$-$C_8$-alkoxycarbonyl or $C_1$-$C_8$-alkanoyl;

$R_4$ is hydrogen, $C_1$-$C_8$-alkyl, $C_1$-$C_8$-alkoxycarbonyl or $C_1$-$C_8$-alkanoyl;

$R_5$ are each independently hydrogen or $C_1$-$C_8$-alkyl, $R_6$ is oxygen,

R is heterocyclyl bonded via a ring nitrogen atom, in which case the heterocyclyl mentioned, apart from the ring nitrogen atom via which it is bonded, may contain further ring heteroatoms selected from oxygen, nitrogen, nitrogen substituted by lower alkyl, lower alkanoyl, (lower alkane)sulphonyl or (lower alkoxy)carbonyl, sulphur, and sulphur bonded to 1 or 2 oxygen atoms, or salt or prodrug thereof, or where one or more atoms are replaced by their stable, non-radioactive isotopes.

3. A compound according to claim 1 of the formula I, where R is a group of the formula

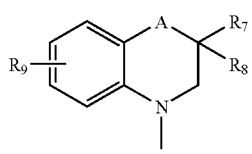

(Ia)

in which

A is a direct bond, methylene, dimethylene, imino, oxy or thio, $R_7$ is $C_1$-$C_4$-alkoxy-$C_1$-$C_4$-alkyl, such as methoxy- or propyloxymethyl, $C_3$-$C_5$-alkenyloxy-$C_1$-$C_4$-alkyl, such as allyloxymethyl, $C_1$-$C_4$-alkoxy-$C_1$-$C_4$-alkoxy-$C_1$-$C_4$-alkyl, such as methoxymethoxymethyl or 2-methoxyethoxymethyl, $C_1$-$C_4$-alkoxycarbonylamino-$C_1$-$C_4$-alkyl, such as methoxy- or ethoxycarbonylaminomethyl, $C_1$-$C_4$-alkoxyimino-$C_1$-$C_4$-alkyl, such as methoxyiminomethyl, phenyl, $C_1$-$C_4$-alkoxycarbonyl, such as methoxycarbonyl, ethoxycarbonyl or isopropyloxycarbonyl, cyano, carbamoyl, N—$C_1$-$C_4$-alkylcarbamoyl, such as N-methylcarbamoyl, N-ethylcarbamoyl or N-butylcarbamoyl, $C_1$-$C_4$-alkoxy-$C_1$-$C_4$-alkylcarbamoyl, such as N-(2-methoxyethyl)carbamoyl, $C_1$-$C_4$-alkoxy such as propyloxy, $C_1$-$C_4$-alkoxy-$C_1$-$C_4$-alkoxy such as methoxymethoxy or 2-methoxyethoxy, $C_1$-$C_8$-alkanoyloxy such as acetoxy, benzoyloxy, N—$C_1$-$C_4$-alkylcarbamoylamino, such as N-methylcarbamoylamino, $C_1$-$C_4$-alkanoylamino, such as acetylamino, $C_1$-$C_4$-alkoxycarbonylamino, such as methoxycarbonylamino, 3- to 6-membered cycloalkylcarbonylamino, such as cyclopropylcarbonylamino, $C_1$-$C_4$-alkoxy-$C_1$-$C_4$-alkanoylamino, such as methoxyacetylamino, or 5- or 6-membered N,N-(1-oxo(lower alkylene))amino or N,N-(1-oxo-2-oxa(lower alkylene))amino, such as 2-oxopyrrolidin-1-yl or 2-oxooxazolidin-3-yl, N—$C_1$-$C_4$-alkyl-carbamoylamino, such as methylcarbamoylamino, $R_8$ is hydrogen, but may also be $C_1$-$C_4$-alkyl such as methyl, and $R_9$ is hydrogen or halogen.

4. A compound according to claim 1 of the formula

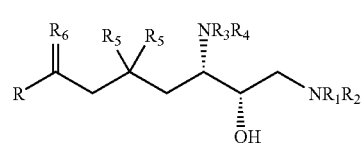

(Ic)

where R, $R_1$, $R_2$, $R_3$, $R_4$, $R_5$ and $R_6$ are each as defined in claim 1 or salt thereof, in particular pharmaceutically usable salt thereof.

5. A compound according to claim 1 of the formula

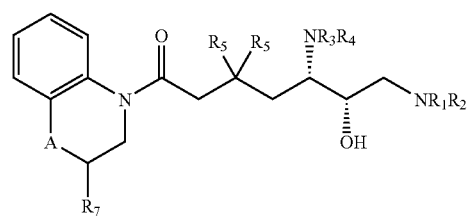

(Id)

where

A is methylene, oxy or thio, $R_1$ is a) hydrogen; or is b) $C_1$-$C_8$-alkyl or $C_3$-$C_8$-cycloalkyl;

$R_2$ is a) $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_3$-$C_8$-cycloalkyl, $C_3$-$C_8$-cycloalkoxy, $C_{1-6}$-alkylamino, cyano, halogen, hydroxyl, oxide, $C_0$-$C_6$-alkylcarbonylamino, $C_1$-$C_8$-alkoxy, oxo, trifluoromethyl or aryl; or b) together with $R_1$ and the nitrogen atom to which they are bonded, is a saturated or partly unsaturated, 4-8-membered heterocyclic ring which may contain an additional nitrogen or oxygen atom, in which case the additional nitrogen atom may optionally be substituted by $C_1$-$C_8$-alkyl or $C_1$-$C_8$-alkanoyl, and this heterocyclic ring may be part of a bicyclic or tricyclic ring system having a total of up to 16 members, and the second ring may also contain a nitrogen or oxygen atom, in which case the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, cyano, oxide, oxo, $C_1$-$C_8$- alkoxy, $C_1$-$C_8$-alkoxy-$C_1$-$C_8$-alkoxy, $C_0$-$C_8$-alkylcarbonylamino, $C_1$-$C_8$-alkoxycarbonylamino or aryloxy-$C_0$-$C_4$-alkyl-$C_1$-$C_8$-alkoxy;

$R_3$ is hydrogen or —(C═O)—$C_1$-$C_4$-alkyl;

$R_4$ is hydrogen;

are each independently $C_1$-$C_4$-alkyl, such as methyl, $R_7$ is $C_1$-$C_4$-alkoxycarbonylamino such as methoxycarbonylamino, ethoxycarbonylamino, propyloxycarbonylamino, isopropyloxycarbonylamino or butyloxycarbonylamino, $C_1$-$C_4$-alkoxy-$C_1$-$C_4$-alkoxy-$C_1$-$C_4$-alkyl, such as methoxy-$C_1$-$C_4$-alkoxy-$C_1$-$C_4$-alkyl, ethoxy-$C_1$-$C_4$-alkoxy-$C_1$-$C_4$-alkyl, propyloxy-$C_1$-$C_4$-alkoxy-$C_1$-$C_4$-alkyl, isopropyloxy-$C_1$-$C_4$-alkoxy-$C_1$-$C_4$-alkyl or butyloxy-$C_1$-$C_4$-alkoxy-$C_1$-$C_4$-alkyl, where $C_1$-$C_4$-alkoxy is, for example, methoxy, ethoxy, propyloxy or butyloxy, and $C_1$-$C_4$-alkyl is, for example, methyl, ethyl, propyl or butyl, in particular methoxymethoxymethyl, 2-methoxyethoxymethyl or 3-methoxypropyloxymethyl, $C_1$-$C_4$-alkoxy-$C_1$-$C_4$-alkyl, such as methoxy-$C_1$-$C_4$-alkyl, ethoxy-$C_1$-$C_4$-alkyl, propyloxy-$C_1$-$C_4$-alkyl, isopropyloxy-$C_1$-$C_4$-alkyl, butyloxy-$C_1$-$C_4$-alkyl, isobutyloxy-$C_1$-$C_4$-alkyl, sec-butyloxy-$C_1$-$C_4$-alkyl or tert-butyloxy-$C_1$-$C_4$-alkyl, where $C_1$-$C_4$-alkyl is, for example, methyl, ethyl, propyl or butyl, in particular ethoxymethyl or 2-methoxyethyl, or N—$C_1$-$C_4$-alkylcarbamoyl, such as N-methylcarbamoyl, N-ethylcarbamoyl, N-propylcarbamoyl or N-butylcarbamoyl, or salt thereof, in particular a pharmaceutically usable salt thereof.

6. A pharmaceutical preparation comprising, as an active pharmaceutical ingredient, a compound according to claim 1 in free form or as a pharmaceutically usable salt, and a pharmaceutically inert excipient.

7. A method for the treatment of hypertension, heart failure, glaucoma, cardiac infarction, kidney failure or restenosis in a patient, which comprises administering a therapeutically effective amount of a compound according to claim 1 to a patient in need thereof.

8. A compound according to claim 2 of the formula I, where R is a group of the formula

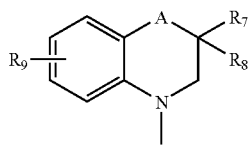

(Ia)

in which

A is a direct bond, methylene, dimethylene, imino, oxy or thio, $R_7$ is $C_1$-$C_4$-alkoxy-$C_1$-$C_4$-alkyl, such as methoxy- or propyloxymethyl, $C_3$-$C_8$-alkenyloxy-$C_1$-$C_4$-alkyl, such as allyloxymethyl, $C_1$-$C_4$-alkoxy-$C_1$-$C_4$-alkoxy-$C_1$-$C_4$-alkyl, such as methoxymethoxymethyl or 2-methoxyethoxymethyl, $C_1$-$C_4$-alkoxycarbonylamino-$C_1$-$C_4$-alkyl, such as methoxy- or ethoxycarbonylaminomethyl, $C_1$-$C_4$-alkoxyimino-$C_1$-$C_4$-alkyl, such as methoxyiminomethyl, phenyl, $C_1$-$C_4$-alkoxycarbonyl, such as methoxycarbonyl, ethoxycarbonyl or isopropyloxycarbonyl, cyano, carbamoyl, N—$C_1$-$C_4$-alkylcarbamoyl, such as N-methylcarbamoyl, N-ethylcarbamoyl or N-butylcarbamoyl, $C_1$-$C_4$-alkoxy-$C_1$-$C_4$-alkylcarbamoyl, such as N-(2-methoxyethyl)carbamoyl, $C_1$-$C_4$-alkoxy such as propyloxy, $C_1$-$C_4$-alkoxy-$C_1$-$C_4$-alkoxy such as methoxymethoxy or 2-methoxyethoxy, $C_1$-$C_8$-alkanoyloxy such as acetoxy, benzoyloxy, N—$C_1$-$C_4$-alkylcarbamoylamino, such as N-methylcarbamoylamino, $C_1$-$C_4$-alkanoylamino, such as acetylamino, $C_1$-$C_4$-alkoxycarbonylamino, such as methoxycarbonylamino, 3- to 6-membered cycloalkylcarbonylamino, such as cyclopropylcarbonylamino, $C_1$-$C_4$-alkoxy-$C_1$-$C_4$-alkanoylamino, such as methoxyacetylamino, or 5- or 6-membered N,N-(1-oxo(lower alkylene))amino or N,N-(1-oxo-2-oxa(lower alkylene))amino, such as 2-oxopyrrolidin-1-yl or 2-oxooxazolidin-3-yl, N—$C_1$-$C_4$-alkyl-carbamoylamino, such as methylcarbamoylamino, $R_8$ is hydrogen, but may also be $C_1$-$C_4$-alkyl such as methyl, and $R_9$ is hydrogen or halogen.

9. A pharmaceutical preparation comprising, as an active pharmaceutical ingredient, a compound according to claim 2 in free form or as a pharmaceutically usable salt, and a pharmaceutically inert excipient.

10. A pharmaceutical preparation comprising, as an active pharmaceutical ingredient, a compound according to claim 3 in free form or as a pharmaceutically usable salt, and a pharmaceutically inert excipient.

11. A pharmaceutical preparation comprising, as an active pharmaceutical ingredient, a compound according to claim 4 in free form or as a pharmaceutically usable salt, and a pharmaceutically inert excipient.

12. A pharmaceutical preparation comprising, as an active pharmaceutical ingredient, a compound according to claim 5 in free form or as a pharmaceutically usable salt, and a pharmaceutically inert excipient.

\* \* \* \* \*